US007932095B2

(12) United States Patent
Herpst

(10) Patent No.: US 7,932,095 B2
(45) Date of Patent: Apr. 26, 2011

(54) SAMPLE HOLDING SUBSTRATE FOR USE WITH AN INFRARED SPECTROPHOTOMETER OR FILTOMETER AND METHODS OF MANUFACTURE AND USE THEREOF

(76) Inventor: Robert D. Herpst, Mahwah, NJ (US)

( * ) Notice: Subject to any disclaimer, the term of this patent is extended or adjusted under 35 U.S.C. 154(b) by 961 days.

(21) Appl. No.: 09/977,664

(22) Filed: Oct. 15, 2001

(65) Prior Publication Data

US 2002/0061597 A1 May 23, 2002

Related U.S. Application Data

(60) Provisional application No. 60/241,223, filed on Oct. 18, 2000, provisional application No. 60/273,275, filed on Mar. 2, 2001.

(51) Int. Cl.
*G01N 21/00* (2006.01)
(52) U.S. Cl. ............... 436/164; 422/401; 422/82.05; 422/561; 356/244; 356/246
(58) Field of Classification Search ............. 422/63, 422/64, 99, 104, 401, 82.05, 561; 436/43, 436/46, 45, 164; 435/282.3, 292.1, 305.1, 435/305.2, 305.3; 356/244, 246
See application file for complete search history.

(56) References Cited

U.S. PATENT DOCUMENTS

| | | | | |
|---|---|---|---|---|
| 4,260,687 A * | 4/1981 | Jacobson et al. | ........... | 435/288.5 |
| 4,843,030 A * | 6/1989 | Eden et al. | ........... | 117/90 |
| 4,855,110 A * | 8/1989 | Marker et al. | ........... | 422/102 |
| 4,932,780 A * | 6/1990 | Izumi | ........... | 356/451 |
| 5,468,606 A * | 11/1995 | Bogart et al. | ........... | 435/5 |
| 5,764,355 A * | 6/1998 | Gagnon et al. | ........... | 356/244 |
| 5,869,345 A * | 2/1999 | Chandler | ........... | 436/514 |
| 6,033,627 A * | 3/2000 | Shields et al. | ........... | 422/58 |
| 6,037,168 A * | 3/2000 | Brown | ........... | 435/288.3 |
| 6,186,403 B1 * | 2/2001 | Ozbey et al. | ........... | 235/487 |
| 6,328,027 B1 * | 12/2001 | Persyk et al. | ........... | 125/21 |

* cited by examiner

*Primary Examiner* — Lyle Alexander
(74) *Attorney, Agent, or Firm* — Roger M. Rathbun

(57) ABSTRACT

A sample card for use in a spectroscopic analytical instrument. The card is preferably disposable and includes an aperture through the card in which there is positioned a sample supporting window on which a sample is adapted to be placed. The sample supporting window is made from a light energy transmitting material by one of the steps such as cleaving, fly cutting, chipping milling, sawing or scaling. A method of manufacturing the card and for using the card are also included where the method includes the step of providing light supporting window by forming that window by the aforedescribed processes.

32 Claims, 15 Drawing Sheets

SAMPLE CARD FRAME WITH 2 APERTURES FOR FOLD OVER
SANDWICHING OF SAMPLE SUPPORT WINDOW

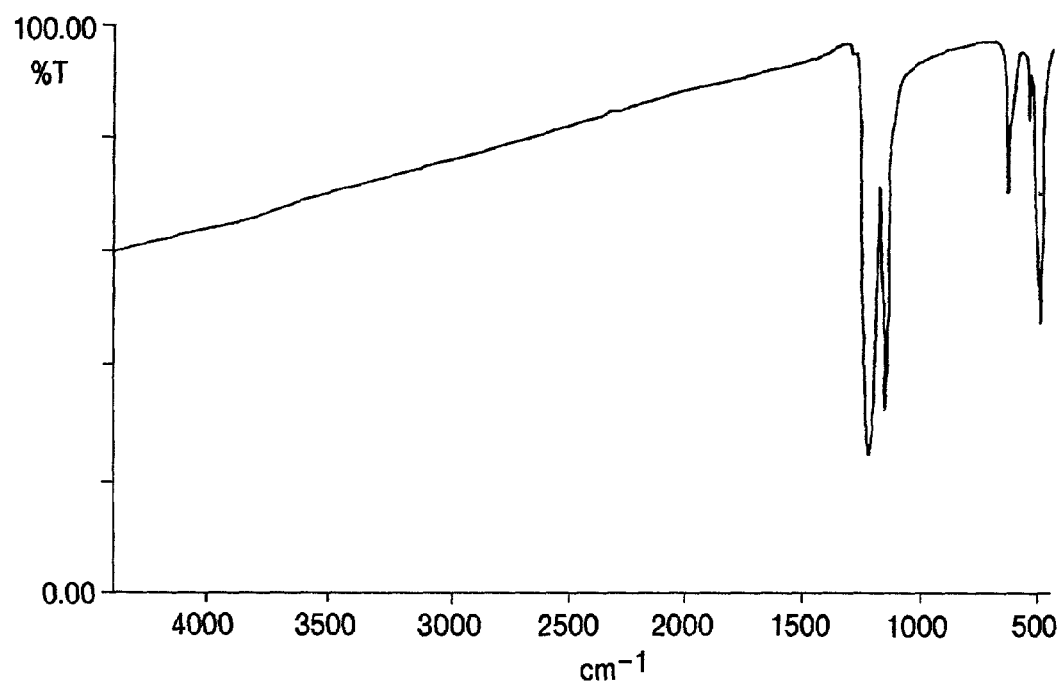
PTFE 3M SAMPLE CARD TRANSMISSION SPECTRUM (TOP)
AND ABSORBANCE SPECTRUM (BOTTOM)
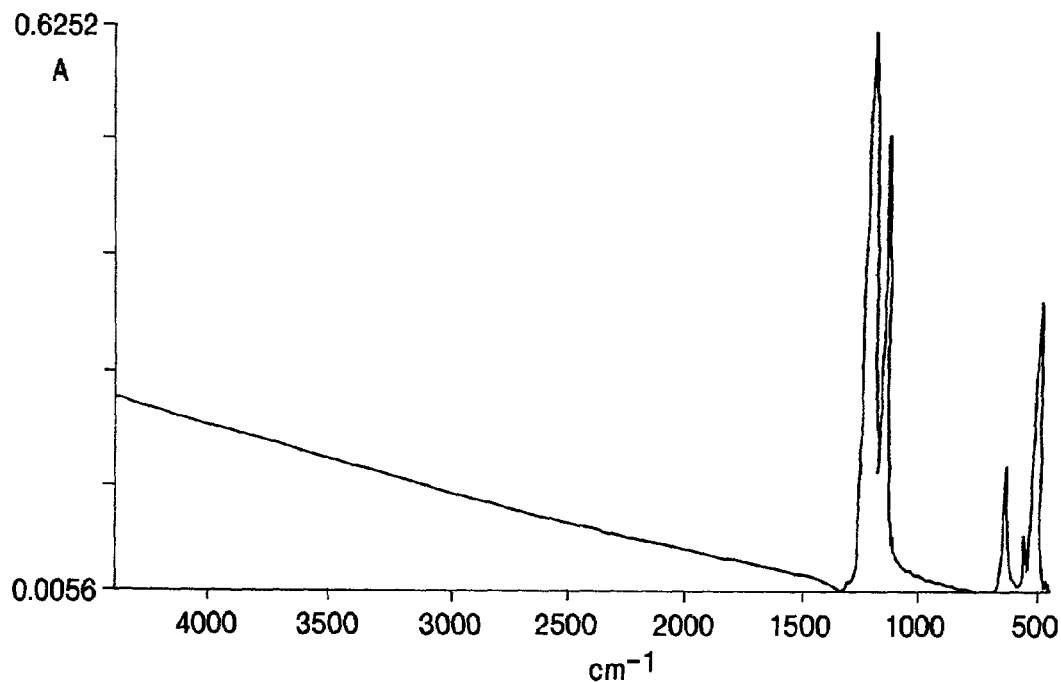
FIG. 1

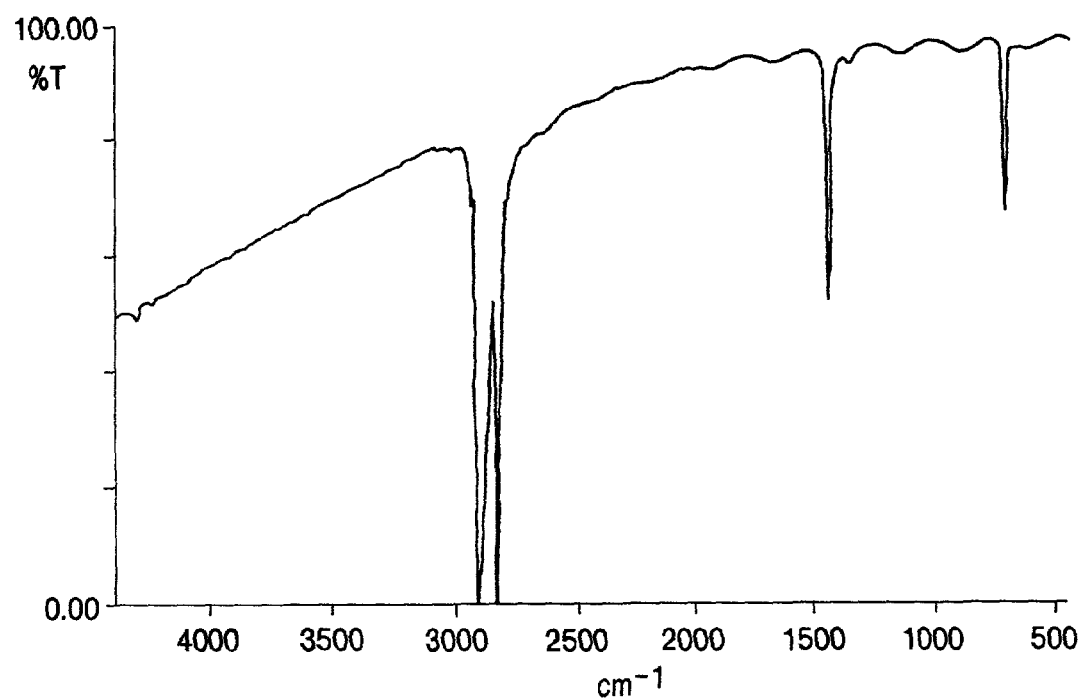
POLYETHYLENE 3M SAMPLE CARD TRANSMISSION SPECTRUM (TOP)
AND ABSORBANCE SPECTRUM (BOTTOM)
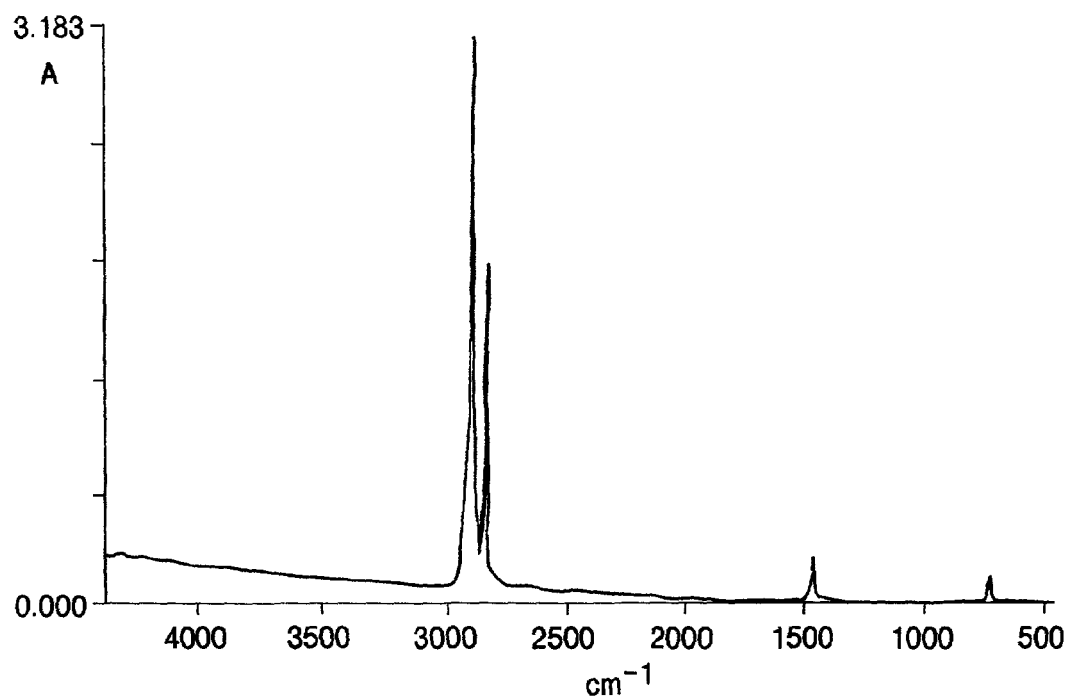
FIG. 2

SPECTRUM KCL CRYSTAL BLANK, UNPOLISHED

SPECTRUM KCL CRYSTAL BLANK, WATER POLISHED

SPECTRUM NACL CRYSTAL BLANK, UNPOLISHED

SPECTRUM NACL CRYSTAL BLANK, WATER POLISHED

SPECTRUM KBR CRYSTAL BLANK, UNPOLISHED

SPECTRUM KBR CRYSTAL BLANK, WATER POLISHED

JANOS SCREEN CARD

3M SAMPLE CARD—PTFE

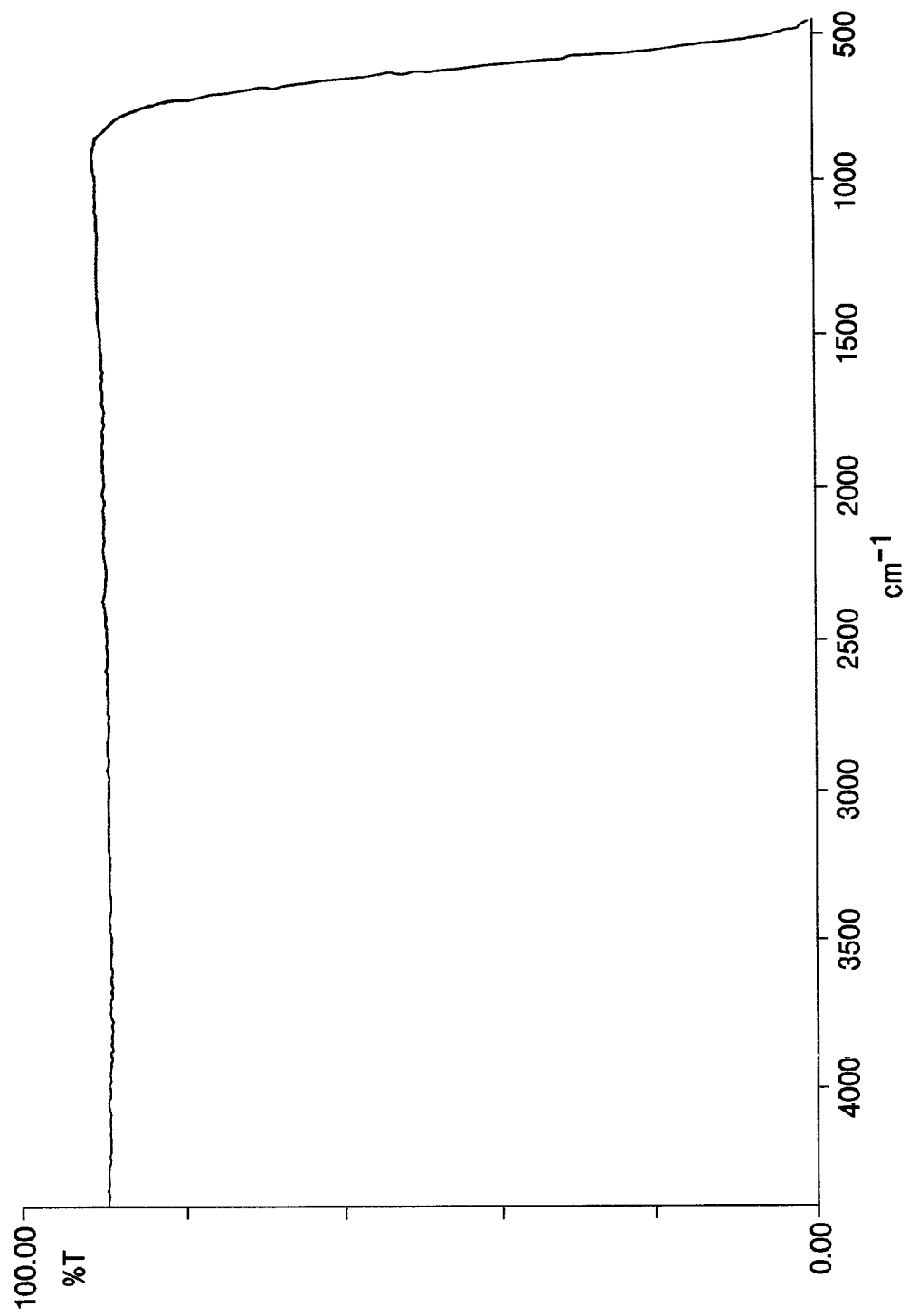

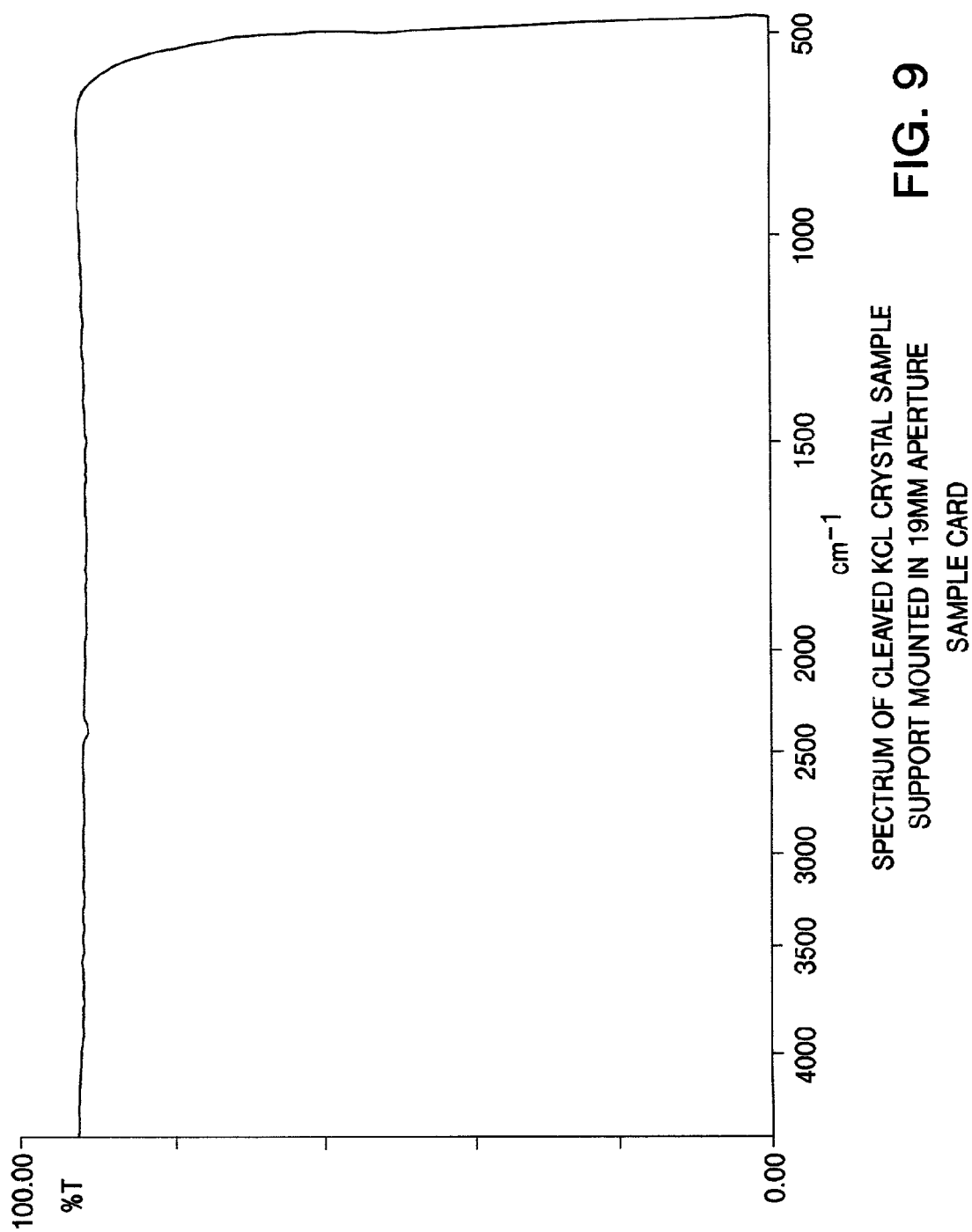

SPECTRUM OF CLEAVED KBR CRYSTAL SAMPLE SUPPORT MOUNTED IN 19MM APERTURE SAMPLE CARD

EXPLODED VIEW OF SAMPLE CARD WITH CLEAVED
CRYSTAL WINDOW AS SAMPLE SUPPORT

SAMPLE CARD FRAME WITH 2 APERTURES FOR FOLD OVER
SANDWICHING OF SAMPLE SUPPORT WINDOW

EXPLODED VIEW OF SAMPLE CARD WITH CLEAVED CRYSTAL AS SAMPLE SUPPORT AND WITH SECOND COVER WINDOW

USE OF SAMPLE CARD IN HORIZONTAL POSITION

SAMPLE HOLDING SUBSTRATE FOR USE WITH AN INFRARED SPECTROPHOTOMETER OR FILTOMETER AND METHODS OF MANUFACTURE AND USE THEREOF

REFERENCE TO RELATED APPLICATIONS

The present application is based upon Provisional Application Ser. No. 60/241,223 filed Oct. 18, 2000 and Provisional Application Ser. No. 60/273,275 filed Mar. 2, 2001.

FIELD OF THE INVENTION

The present invention is a sample holding substrate for holding and orienting a sample in an infrared spectrophotometer or infrared filtometer and a method for the manufacture and use of such sample holding substrate and its component parts, and is directed at providing analysts with an inexpensive sample holding substrate.

BACKGROUND OF THE INVENTION

Spectroscopic analytical instruments are widely used for analysis of samples. As used in herein, the term "spectroscopic analytical instrument" refers to dispersive infrared spectrophotometers ("IR"), Fourier transform infrared ("FTIR") spectrophotometers, fixed band path filtrometers, ultra violet and visible light spectrophotometers ("UV/VIS"), near infrared spectrophotometers ("NIR"), Raman spectrophotometers and any other device used for spectroscopic analysis in which the absorbance by a sample of light energy emitted by the spectroscopic instrument is detected by such instrument. Spectroscopists and other technicians performing analysis by transmission sampling normally place the sample in some type of optically pure sample holding device which positions the sample in the path of the light energy beam emitted by the spectroscopic analytical instrument and allows the energy to be transmitted through the sample without being blocked or absorbed by the sample holder. The instrument's detector then detects the amount of energy absorbed by the sample throughout the region of the spectrum which is within the instrument's range.

When a spectroscopic analytical instrument detects the energy absorbed by the sample, the absorbance is typically represented graphically as vertical peaks shown along the ordinate (y axis) of a graph on which the spectral range is shown as the abscissa (x axis), although absorbance can be represented digitally. Digital readouts are more common for inexpensive instruments such as fixed band pass filtrometers. It is desirable to have a nonabsorbing sample holder so that spurious absorbances from the sample holder do not interfere with the analysis.

IR and FTIR spectrophotometers normally employ sample holders containing high quality crystal optics as sampling substrates, while UV/VIS, Raman and NIR spectrophotometers use sample holders comprised of silica and certain types of silica glass and fused silica compositions. The distinguishing feature of the desirable light energy transmitting materials used in all spectroscopic analytical instruments is that they do not absorb energy in all or a significant part of the spectral region where the instrument operates.

Sample holders using high quality crystal optics which have been shaped and polished by precision opticians for optimum performance are capable of transmitting enough infrared energy in the spectral region of interest to the infrared spectroscopist to enable performance of both qualitative and quantitative analysis of a sample. When performing quantitative analysis by transmission sampling, the infrared spectroscopist can define the thickness of the sample by sandwiching the sample between two crystal windows separated by a spacer. Many infrared spectroscopists also prefer to sandwich the sample between windows when performing qualitative analysis.

In cases where the analysis involves studying the absorbance peaks of a sample which occur in a limited spectral region, the spectroscopist can sometimes tolerate use of a sample holder which absorbs energy in another spectral region as the absorbance peaks created by the sample supporting substrate will not obscure the analysis. It is also possible to compensate to a certain extent for absorbance peaks created by the sample holder by either placing a duplicate sample holder in the compensating beam of a double beam IR spectrophotometer or by running a background with an FTIR spectrophotometer which subtracts or ratios the background from the scan of the sample. Taking a background also compensates for water and $CO_2$ in the atmosphere and for low energy transmission through the sample supporting substrate. But where absorbance peaks are strong, use of backgrounds to ratio those absorbance peaks out of the analysis of the sample becomes an ineffective technique. Rather than to rely upon backgrounds as compensating tools, many infrared spectroscopists prefer to use optically pure sampling supporting windows with high energy throughput and to purge the sample compartment of atmospheric contamination (typically $H_2O$ and $CO_2$) using a dry gas such as nitrogen.

A business unit of Minnesota Mining & Manufacturing Corporation ("3M") introduced a polymer based IR sample card (U.S. Pat. No. 5,764,355) several years ago for use in transmission testing which was available with two sample supporting windows viz. polyethylene & polytetrafluoroethylene ("PTFE"). More recently, another company, Spectra-Tech, has begun manufacturing sample cards with polyethylene and PTFE sampling support windows. Unfortunately, when a spectroscopist does an analysis of a sample applied to a polyethylene or PTFE window, an analysis is being made of both the sample and the window. Both of these sample cards use sampling substrate windows that have strong absorbances in the spectral range of interest for most IR and FTIR spectrophotometers and for other spectroscopic analytical instruments. As shown in FIG. 1, the window in the PTFE card exhibits strong absorbance peaks in the important 1300 to 450 $cm^{-1}$ region (in particular at 1223.6 $cm^{-1}$, 1156.1 $cm^{-1}$, 639.4 $cm^{-1}$, 554.7 $cm^{-1}$, and 502.9 $cm^{-1}$). As shown in FIG. 2, the window in the polyethylene card exhibits strong absorbance peaks at 2918.7 $cm^{-1}$ and 2849.9 $cm^{-1}$ and somewhat less pronounced but still annoying peaks at 1473.1 $cm^{-1}$, 1462.9 $cm^{-1}$, 730.2 $cm^{-1}$ and 719.9 $cm^{-1}$. As noted above, by running a background, certain absorbance peaks can be ratioed or subtracted, but they still complicate the analysis and the high C—F absorbance of the PTFE substrate in the region of 1300 to 450 $cm^{-1}$ and the high aliphatic C—H stretching absorbance of the polyethylene substrate in the 2918-2849 $cm^{-1}$ region makes both cards of somewhat limited utility because running a background with such strong absorbances does not completely ratio out the absorbance peaks. Furthermore, taking backgrounds to compensate for spurious absorbance peaks in the sampling substrate requires a time consuming extra step which may defeat the purpose of using a disposable sample card for a quick qualitative analysis.

Another company, Janos Technology, Inc., currently markets a sample card which uses a screen or mesh as the sampling substrate of the type disclosed in U.S. Pat. Nos. 5,453, 252 & 5,723,341. Although mesh cards do not create absorbance peaks, they do suffer from several deficiencies as sampling substrates. First, the mesh does not retain liquid samples very well in the vertical position. The aforesaid patents state that using the preferred mesh size for the screen sampling substrate will result in a contiguous film for about 10 seconds, which is too short a time to run more than a few scans on an FTIR spectrophotometer and is too short to complete even a single scan on a plotting dispersible IR spectrophotometer. In addition, there are frequently voids in mesh card samples. Furthermore, liquid samples applied to mesh form a meniscus at the interface of the mesh lattice with the liquid which makes the sample thicker in some places than it is in others. Many liquid samples analyzed by IR or FTIR spectroscopy are solutions which reach a viscoelastic state and then solidify into films. It is often preferable to allow the solvent in such a sample to evaporate, leaving a dry sample film of the solute. The remaining dry cured film is then analyzed by placing it in the beam of the spectrophotometer either on a transmissive substrate or as a free standing film. This method eliminates the complication of analyzing both the solvent and the solute. If the surface tension of the film on a screen or mesh sampling substrate is overcome by gravity within 10 seconds, many films will break before they can solidify. Similarly, mesh sampling substrates are not well suited for analysis of weakly absorbing solutions which do not reach a viscoelastic state, as when the solvent is evaporated the remaining sample is not dispersed evenly over the sampling supporting substrate. Another shortcoming of mesh sample support substrates is that when the preferred mesh size is used, only 50% of the energy available from the spectrophotometer is transmitted. This is sufficient for analysis of many samples, but many spectroscopists prefer more efficient energy throughput and prefer not to have to run a background to adjust for the lower energy throughput simply to make the spectra obtained more readable. Backgrounds take time to run and they cannot be run on all spectroscopic analytical instruments.

Spectroscopists have, for many years, used polished crystals and unpolished crystal blanks to perform qualitative and quantitative analysis of liquid and solid samples with IR and FTIR spectroscopic analytical instruments. Polished crystal windows are expensive and are, therefore, not at all comparable to disposable sample cards with polymer or mesh sample supporting windows. These precision polished windows are typically used within cells for quantitative and qualitative analysis.

On the other hand, unpolished crystal windows, known as "blanks", are relatively inexpensive and are used for the same purpose as IR sample cards. Crystal blank windows used as sampling substrates are typically made from alkali halide crystals, such as KBr, NaCl and KCl. An unpolished alkali halide window will not exhibit any spurious absorbance peaks when the infrared beam of a spectrophotometer is passed through the window and the instrument is set at normal detection limits. Energy transmission of halide blanks is enhanced by a quick water polish which can be done by the spectroscopist with minimal equipment.

As can be seen in FIGS. 3A, 3B, 4A, 4B, 5A, and 5B, the transmission of these materials is enhanced measurably by water polishing. Neither training as an optician nor special equipment are required to water polish NaCl or KCl blanks. They can be effectively water polished by rubbing them on a paper towel on which a water and alcohol solution has been deposited on part of the towel. The crystal blank is simply rubbed alternately on the wet area of the towel and then back onto the dry area until adequate transparency is achieved. KBr blanks are water polished using the same technique, but the blanks must first be conditioned on a soft optical polishing cloth with the proper polishing compound. The polishing cloths and compounds are sold in inexpensive polishing kits that can be obtained from vendors of spectroscopy optics. A water polished KCl blank will transmit well in excess of 90% of the of the available energy over the range of 4400 $cm^{-1}$ to 500 $cm^{-1}$ (See FIG. 3B), while water polished NaCl and KBr blanks transmit in excess of 85% of the available energy in the ranges, respectively, of 4400 $cm^{-1}$ to 666 $cm^{-1}$ and 4400 $cm^{-1}$ to 450 $cm^{-1}$ (See FIGS. 4B & 5B).

Crystal blanks make more desirable sample supporting windows than sample cards using PTFE or polyethylene as windows, because the crystal windows have transmission and absorbance properties superior to polymers. Furthermore, windows made from crystal blanks can be used in pairs to create sandwich cells and can be used to efficiently cast films from solutions. Unfortunately, crystal blanks cost 2.5 to 4 times what a polymer sample card will cost and the crystal blank windows also require use of a holder to orient them in the spectrophotometer beam. The number of samples that can be scanned on a water polished crystal blank far exceeds the single sample scan that is taken with a disposable sample card made with mesh or polymer windows, because it is possible to repolish crystal blanks. Spectroscopists have repolished crystal windows for years, however, many labs now consider the labor cost of repolishing a crystal blank window to be too high to justify the effort.

To process an alkali halide crystal into a blank requires several operations in an optical shop. First, a crystal boule must be grown in a furnace. The boule is tested after a growth cycle spanning several days to determine if the requisite optical purity has been achieved. If the boule passes the purity test, it is then annealed. An external dimension must then be created. The external dimension is usually dictated by the size and type of holder in which the optic will be used. The holder is required to orient the [optic] window as a sample supporting substrate in the beam of a spectrophotometer. In the case of a circular crystal window or disc, for example, the external dimension is the diameter and the process of shaping the diameter begins by core drilling the crystal boule and then centerless grinding the rod into its final diameter. Individual disc shaped pieces are then cut from the rod. An alternative is sawing or cleaving the material into individual pieces and then edging the outside diameter of each piece. The faces of the disc are then lapped in stages on optical lapping machines using grinding compounds with progressively smaller particles. The lapping process causes the crystal to become opaque when it is ground with courser grinding compounds. Unless the opacity is overcome by a fine polish using smaller size grinding compounds or by a water polish (as discussed earlier), the opacity of the optic dramatically limits the ability of the optic to transmit light energy (including the infrared energy used in an IR or FTIR spectrophotometer). At each stage the optics are cleaned; first, to keep larger particulate grinding compound from contaminating smaller particulate stages of the process and next, to remove the finest grinding compound and chemicals in the grinding compound carrier slurry. This multi-step process is labor intensive and expensive, which is one of the reasons that crystal blanks are more expensive sample supporting windows than polymers or screens and mesh.

For many years infrared spectroscopists have pressed windows known as "pellets" of a matrix of KBr and a solid sample to produce spectra of the solid sample. Unfortunately, production of pressed windows from powders requires a number of labor intensive steps and the powders require careful preparation and handling. Contamination of the windows during the pressing process is difficult to avoid when mass production is contemplated. As such, although an adequate window can be pressed from powders, only a few materials which are capable of transmitting infrared energy, such as silver chloride and zinc sulfide, are well suited to pressing. These materials are relatively expensive. Cheaper materials, such as KBr and NaCl, can be pressed into ½' diameter pellets with some success, but as the pressed window diameter gets larger the success rate drops. Pressed windows that are in the 20 to 25 mm diameter range require high pressure, laborious preparation and elaborate precautions against contamination. The resulting windows rapidly absorb moisture which causes them to fog or haze over and they quickly reach the point where energy transmission becomes marginal. Producing a low cost sample supporting window for use in a sample card using this technology is therefore simply not practical.

The use of sample cards for spectroscopic sampling is known in the art. As noted above, 3M produced sample cards which utilized PTFE and polyethylene windows as sample support substrates but it has since discontinued the manufacture of the cards and other vendors have begun to manufacture them. The polymer sample supporting windows do, however, exhibit the undesirable absorbance peaks referenced above which limit their utility. Another similar device is the mesh or screen card in which a liquid sample adheres to the mesh and the beam of the spectrophotometer can pass through the free standing sample. The screen cards exhibit less than optimal energy transmission, the length of time that they will support liquid samples is quite short, and they do not provide a useful platform for sampling solutions. Neither type card can be used to sandwich a sample. Both sample cards are inferior in performance to unpolished crystal blanks. But, both of these sample cards also have the advantage of being inexpensive enough to be disposable and of providing their own sample holder in the form of a cardboard frame for mounting and orienting the sample in the beam of the spectrophotometer on which the spectroscopist can write information regarding the sample as shown in FIG. 7, which makes them convenient to use in the lab.

It would be an advance in the art to provide a sampling device with the convenience and low cost of the polymer window and screen sample cards, but with the superior optical and physical properties of water polished crystal blank windows.

SUMMARY OF THE INVENTION

The invention is directed to a method and apparatus for holding and orienting samples in the light energy beam of spectroscopic analytical instruments. A crystal or other light energy transmitting material sample supporting window material is prepared by cutting the window material, it being understood that by "cutting", it is intended to cover various individual techniques for preparing the surface of the window material without using an abrasive grinding or polishing medium, including, but not limited to: cutting, chipping, milling, cleaving, fly cutting, sawing and scaling of the material. In the preferred embodiment, the sample support substrate window material is an alkali halide crystal such as KBr, NaCl or KCl.

A particularly advantageous feature is that the surface of the window material, albeit somewhat rough, does not need to be laboriously polished or prepared in order to transmit an adequate amount of energy to be useful for spectroscopic analysis. Therefore, the cost of producing the crystal or other light energy transmitting window, as well as the overall sample card, is economical. Even though time consuming and costly processes for preparation of the substrate are not required, the sample supporting window prepared in accordance with the within invention does not absorb energy in the spectral region used for spectroscopic analysis and therefore the substrate does not interfere with the analysis. In addition, dimensionally precise accuracy is not necessary to define the edges or perimeter of the window as the window is preferably mounted on a disposable card of a cellulose material, such as cardboard, and the window is located within an aperture formed in that card while the card masks the edges or perimeter of the window.

In one embodiment of the invention, a sample card comprises two cardboard frames with one or more apertures in each of the frames and wherein there is sandwiched therebetween, a crystal window manufactured in accordance with the present invention and which fills each aperture. The card is used to frame and support the window and to mount it in the spectroscopic analytical instrument and orient or position a sample that has been deposited on the windows within the beam emitted by the spectroscopic analytical instrument. It is understood that such a sample card could be in a carousel shape with windows mounted in apertures located in one or more circular patterns in the frames so that the card can be rotated around a central point within a spectroscopic analytical instrument such that individual samples deposited on each window can be rotated into the beam of the instrument by automation means.

In another preferred embodiment of the invention, a sample card is comprised of a single piece of cardboard with mirror image sides with each such side containing one or more apertures. A spine or fold line centrally located in the card allows one mirror image side to be folded over the other mirror image side in book like fashion. When the card is folded one or more sample supporting substrate windows are sandwiched between the two halves of the card so as to fill each aperture in the card and the card also frames the window. It is understood that such a sample card could be in a carousel shape with windows mounted in apertures located in one or circles in the frame so that the card could be rotated around a central point within a spectroscopic analytical instrument such that individual samples deposited on each window can be rotated into the beam of the instrument by automation means.

In yet another preferred embodiment, a cover slide window is held over a sample which has been applied to the sample supporting window mounted in a cardboard sample card in the manner described above, so that the sample is sandwiched between the two windows. It is understood that the cover slide window may be made by cutting means as herein described or by traditional optical polishing means. It is further understood that a sample card with a carousel configuration, a carousel style sample card or sample cards mounted in a carousel configuration, may be used with automation means to rotate multiple samples into the beam of a spectroscopic analytical instrument and that such samples may be sandwiched between sample supporting windows in the card or cards and cover slide windows.

In use of the present invention, a sample to be analyzed is deposited on the card and the card is positioned either vertically with the window and sample within the beam of the instrument or horizontally with the window and sample within the path of a beam that is reflected through the window.

BRIEF DESCRIPTION OF THE DRAWINGS

The following drawings in which like reference characters indicate like parts are illustrative of embodiments of the present invention and are not intended to limit the invention as encompassed by the claims forming part of the application.

FIG. 1 is the transmission spectrum and the absorbance spectrum of a prior art sample card having a polytetrafluoroethylene window sample supporting substrate;

FIG. 2 is a transmission spectrum and the absorbance spectrum of a prior art sample card having polyethylene window sample supporting substrate;

FIG. 8 is a spectrum of a cleaved NaCl crystal sample made in accordance with the present invention;

FIG. 9 is a spectrum of a cleaved KCl crystal sample made in accordance with the present invention;

DETAILED DESCRIPTION OF THE INVENTION

Turning first to FIG. 1, there is shown the transmission spectrum and the absorbance spectrum of a prior art sample card having a polytetrafluoroethylene ("PTFE") sample supporting window. As can be seen from the Figure, there are strong absorbance peaks in an important spectral region, that is, in the range of 1300 to 450 cm$^{-1}$ (in particular at 1223.6 cm$^{-1}$, 1156.1 cm$^{-1}$, 639.4 cm$^{-1}$, 554.7 cm$^{-1}$, and 502.9 cm$^{-1}$). As will also be noted, the spectral range illustrated in FIG. 1 and the other spectra referred to herein are directed to the infrared range, that is wavelengths from about 4400 cm$^{-1}$ to about 450 cm$^{-1}$ and that range will be used herein to describe the spectral ranges of "infrared light" and also to describe the infrared light that transmits through, or is absorbed by, a sample analyzed by an infrared spectrophotometer or filtometer. Accordingly, as used herein, the term infrared spectral range will refer to the infrared wavelengths from about 4400 cm$^{-1}$ to about 450 cm$^{-1}$.

In FIG. 2 there is also a spectrum for a prior art sample card having a polyethylene sample supporting window, and, again it can be seen that there are strong absorbance peaks at 2918.7 cm$^{-1}$ and 2849.9 cm$^{-1}$ and somewhat less pronounced but still annoying peaks at 1473.1 cm$^{-1}$, 1462.9 cm$^{-1}$, 730.2 cm$^{-1}$ and 719.9 cm$^{-1}$.

While FTIR spectrophotometers are capable of ratioing or subtracting absorbance peaks detected in background scans of sample supporting windows, these techniques complicate the analysis and they are not effective in cases where the absorbance peaks are dramatic. Furthermore, some spectroscopic analytical instruments do not have the capability to ratio background absorbances out of sample spectrum. The absorbances detected in both the PTFE and polyethylene sample supporting windows are too distinct to be effectively ratioed out by taking a background scan of the substrate with an FTIR spectrophotometer, and they make it impossible to use these cards in the full spectral range of a dispersive IR spectrophotometer.

Figure 3A:
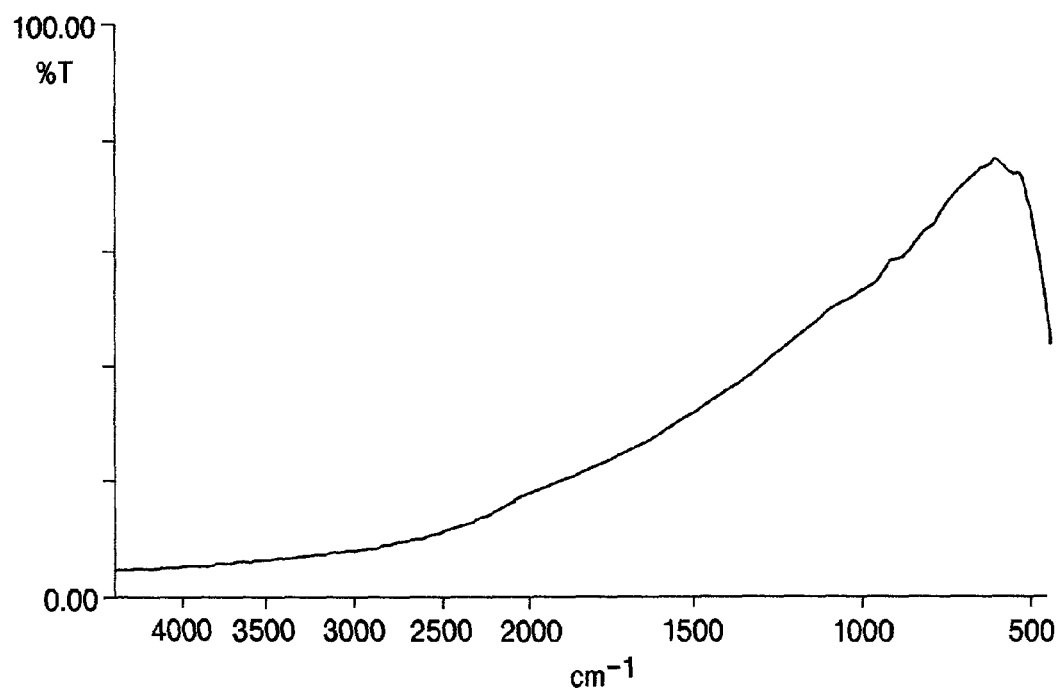
FIG. 3A is a spectrum of a KCl crystal blank in its unpolished form.
Figure 3B:
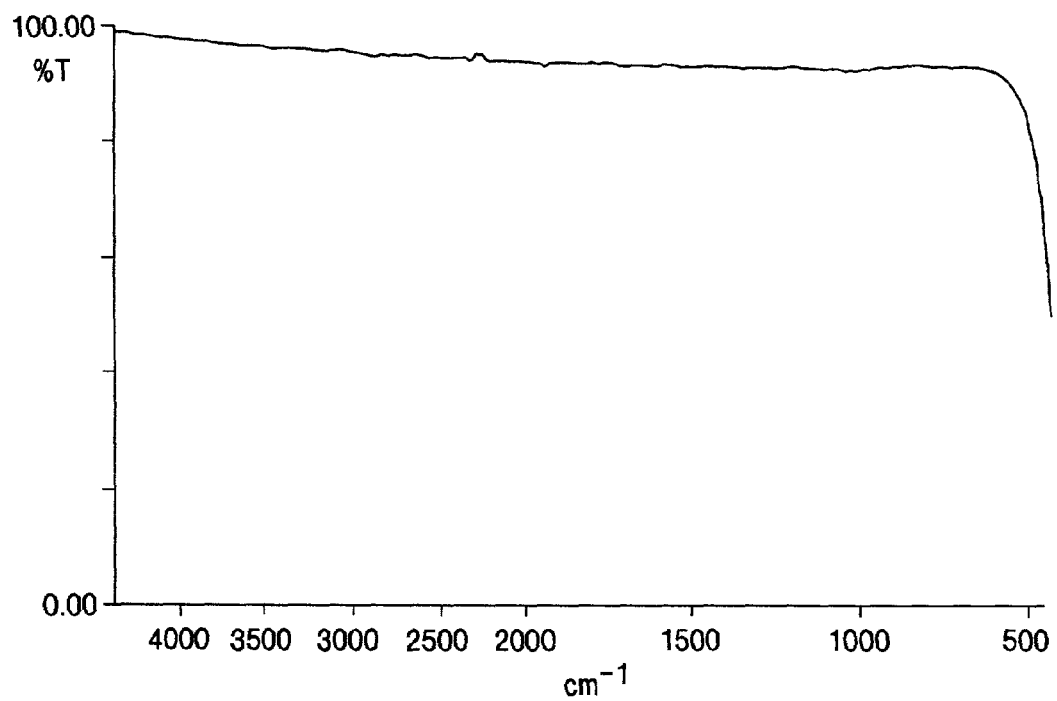
FIG. 3B is a spectrum of a KCl crystal blank that has been water polished.

Turning now to FIGS. 3A and 3B, there are shown comparative spectra contrasting the energy transmission of a KCl crystal blank window in its unpolished form (FIG. 3A) and after the window has gone through the polishing process. It can be seen that polishing the window considerably enhances transmission of infrared energy. The polishing process, as explained, is simply carried out by water polishing the crystal blank by means of rubbing the window on a paper towel having a portion that has been wet with a water and alcohol solution. The crystal blank window is rubbed alternatively on the wet area of the paper towel and then on the dry area until adequate transparency is achieved.

Figure 4A:
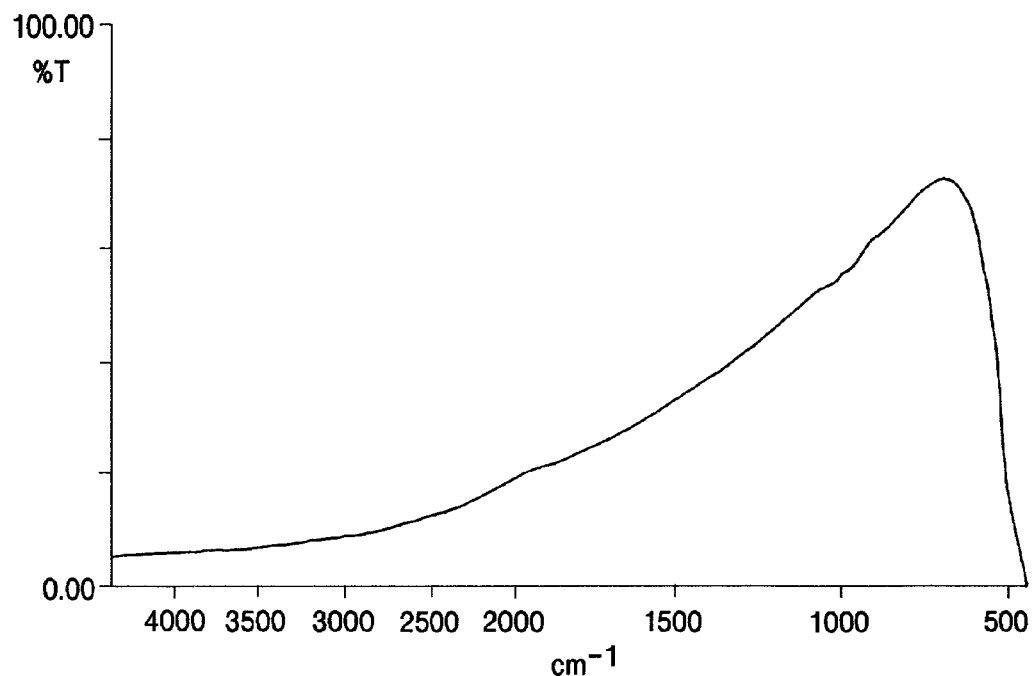
FIG. 4A is a spectrum of a NaCl crystal blank in its unpolished form.
Figure 4B:
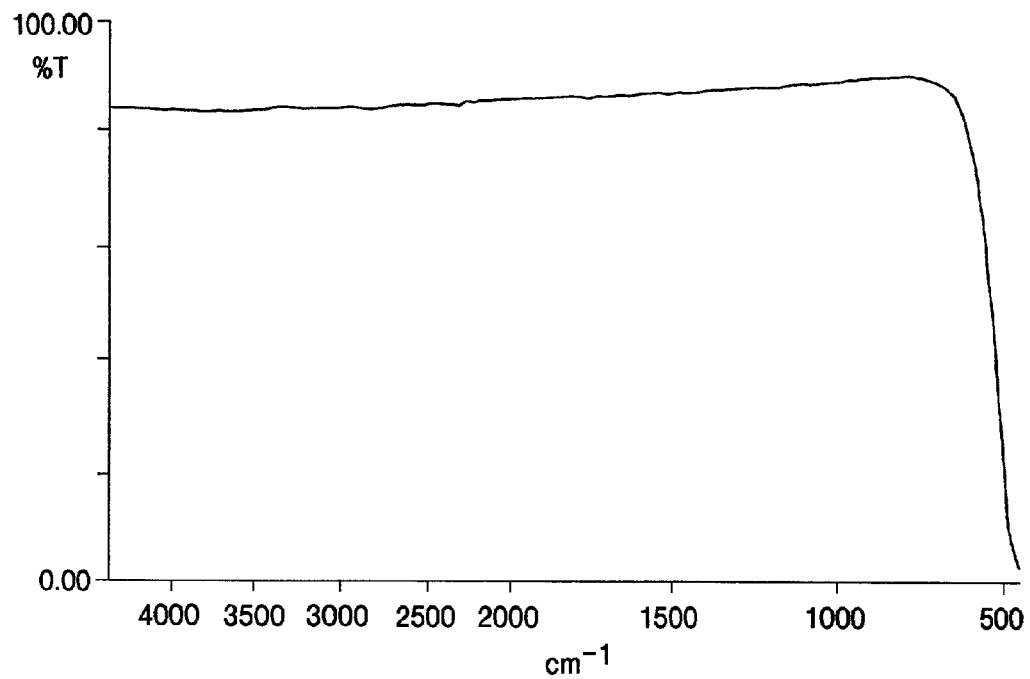
FIG. 4B is a spectrum of a NaCl crystal blank that has been water polished.
Figure 5A:
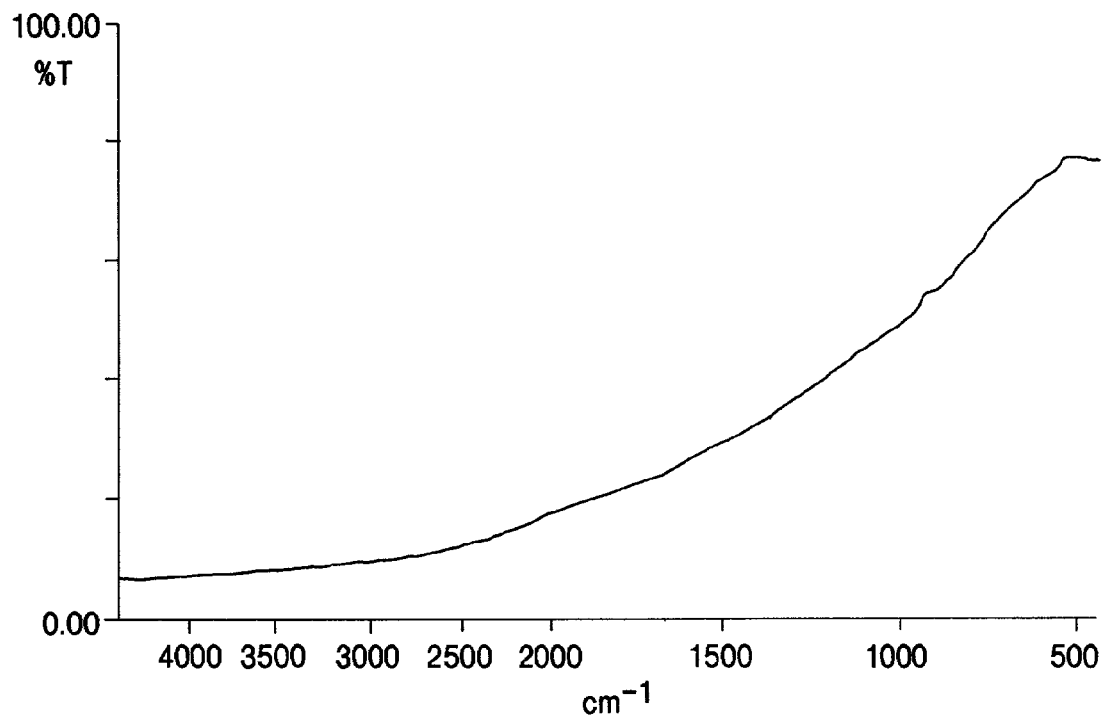
FIG. 5A is a spectrum of a KBr crystal blank in its unpolished form.
Figure 5B:
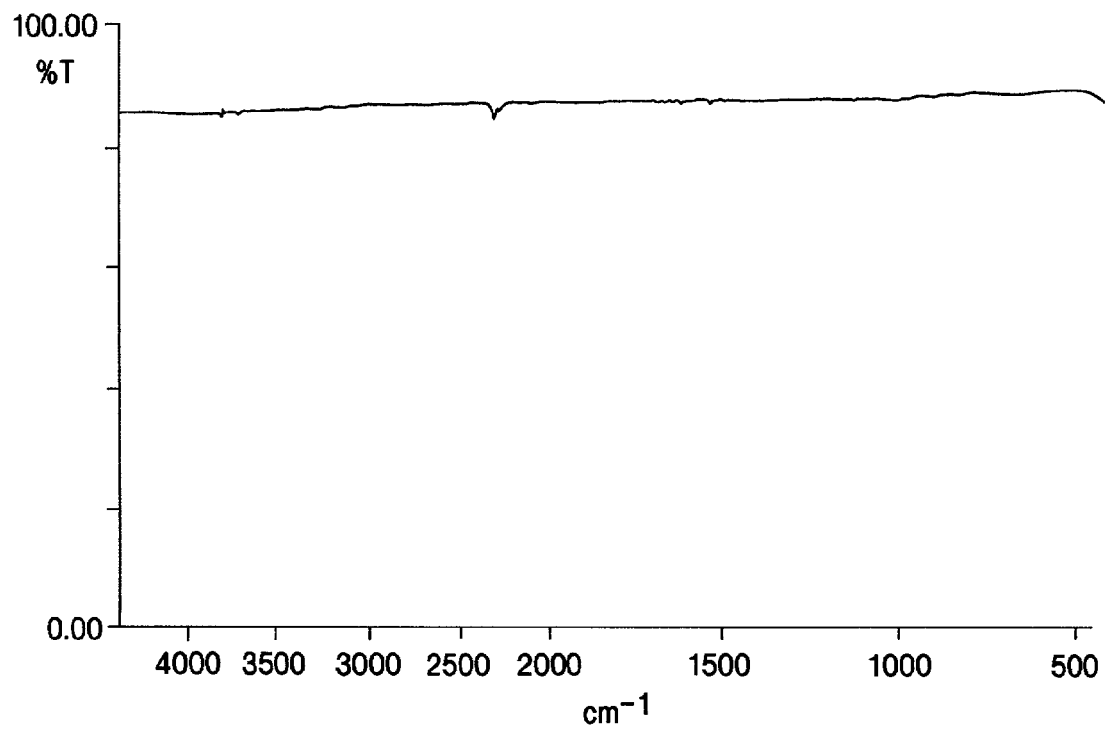
FIG. 5B is a spectrum of a KBr crystal blank that has been water polished.

The same comparison is made in FIGS. 4A and 4B where the window material is NaCl and the same polishing process has been used to improve the transmission of the window from the unpolished material in FIG. 4A to the polished material in FIG. 4B. In FIGS. 5A and 5B, the same comparison is made for a KBr crystal blank, however the polishing technique with the KBr also includes a preconditioning of the crystal blank on a soft optical polishing cloth with a proper polishing compound.

Figure 6:
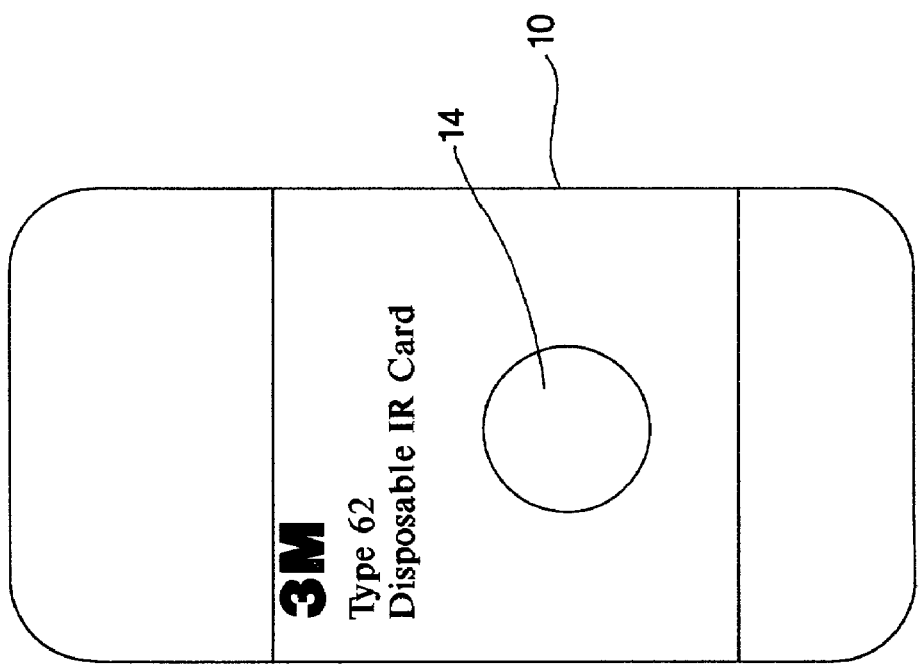
FIG. 6 is a front view of a prior art disposable sample card.

Turning now to FIG. 6, there is shown a sample card 10 that is a prior art example of the sample card 10 that was available from 3M Company and which had a PTFE sample supporting window 14. As noted above, however, the distinct absorbance peaks created by the PTFE window interfere with the desired analysis in the spectral region where the absorbances of the PTFE window are detected.

Figure 7:
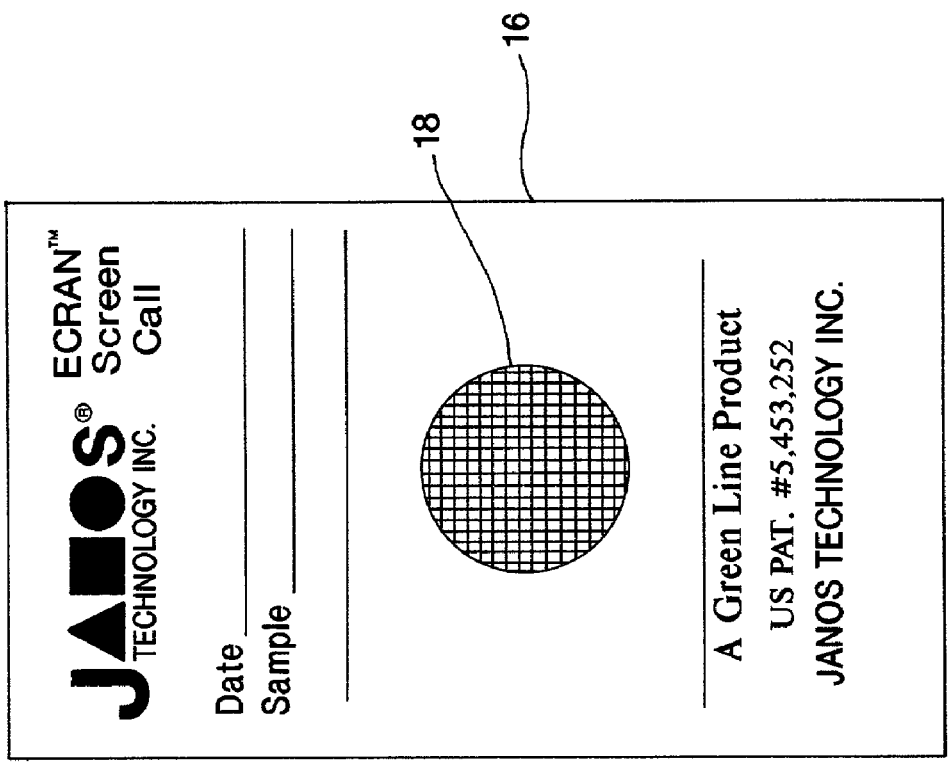
FIG. 7 is a front view of a further prior art screen sample card.

Next, in FIG. 7, there is another type of prior art sample card 16 that includes a mesh or screen 18 sample supporting window on which the sample to be analyzed is deposited. However, as explained previously, the use of a screen 18 is not advantageous where liquids are being analyzed as the liquid is not retained well when the sample card 16 is in a vertical orientation and also, typically, the thickness of the sample varies at localized areas across the screen as a result of meniscuses forming where the wire lattice of the screen interfaces with the sample.

As can be seen, however, sample cards 10, 16 of the cardboard type as shown in FIG. 6 and FIG. 7 offer real conveniences for laboratory applications, inasmuch as: (i) the cards are inexpensive and therefore disposable; (ii) the user can write information relative to the particular sample on the face of the sample card; and (iii) the cards are designed to be inserted directly into the standard slide mount found in most spectrophotometers without the need for additional mounting apparatus to orient the sample in the beam of the instrument.

Figure 10:
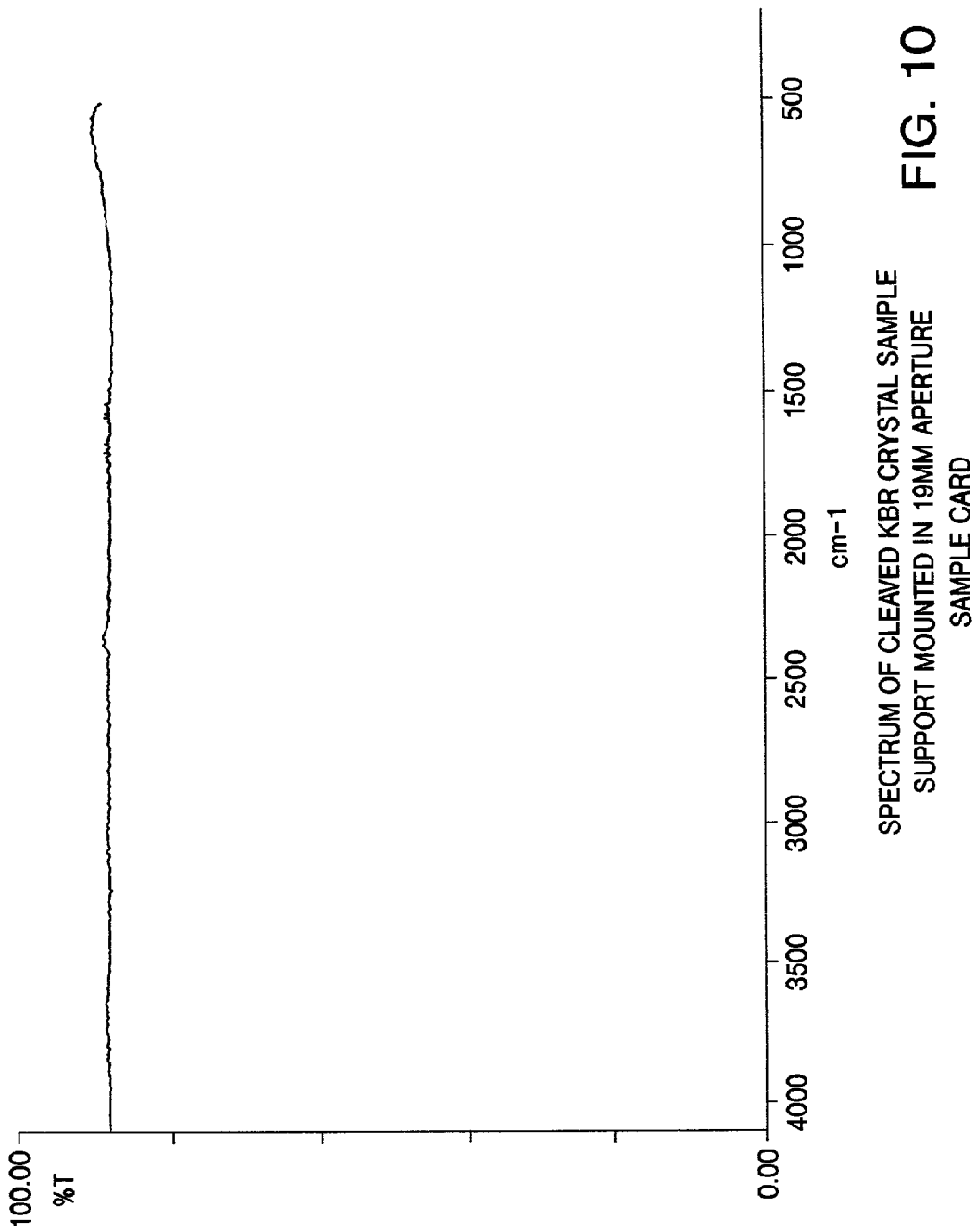
FIG. 10 is a spectrum of a cleaved KBr crystal sample made in accordance with the present invention.

Turning now to FIG. 8, there is shown a spectrum of a cleaved NaCl crystal sample supporting window made in accordance with the present invention, while FIGS. 9 and 10 further illustrate the spectra of cleaved sample supporting windows of KCl and KBr, respectively. All of the crystal sample supporting windows of FIGS. 8-10 were mounted in a 19 mm aperture sample card.

The KBr, KCl and KBr crystal sample supporting windows referenced in FIGS. 8, 9 and 10 were all formed in accordance with the present invention by the known process of cleaving; however, in accordance with the present invention, other mechanical impacting or cutting methods can be used to make the windows, such as fly cutting, chipping, milling, sawing and scaling, it being important that the window has its surface shaped by a mechanical means, not by use of an abrasive compound, and such mechanical means will collectively be referred to herein as "cutting".

Use of frames that serve the dual functions of both holding the sample supporting window and positioning the window and the sample in the beam of the spectrophotometer eliminates the need to form a precise edge on the window. The apertures in the two frames between which the sampling substrate is sandwiched define the boundaries of the sample supporting window and provide a neat finished appearance. Accordingly, from a cosmetic perspective, the sample supporting window can be rectangular, round, oval or irregularly shaped. And, since the frame properly positions the sample supporting window in relationship to the beam of the spectrophotometer, the functional reason for shaping the outside dimension of the sampling substrate (viz. to fit it in a sample holder) is eliminated.

Pieces cut from crystal boules or which are processed by cutting means, which do not cause opacity, such as cleaving, fly cutting, chipping, milling, sawing or scaling, will have sufficient transparency to enable their use as sample supporting windows for use in analysis of samples with spectroscopic analytical instruments. These processing techniques can be used with infrared transmitting crystals such as NaCl, KCL and KBr and also with other light energy transmitting materials such as AMTIR and fused silica. AMTIR is an acronym for "amorphous material transmitting infrared radiation" and commercially available forms of the material include glass compositions of germanium arsenic and selenium (GeAsSe) and germanium, antimony and selenium (GeSbSe). Experimental work with these processes demonstrate that they do not cause the crystals to become opaque as is the case where it is ground in the normal lapping and polishing processes.

As shown in FIGS. 8, 9 and 10, cleaved windows of NaCl, KCl and KBr, respectively, sandwiched between 2"×3" paper cards with a 19 mm aperture transmit in excess of 80% of the available energy emitted by an FTIR spectrophotometer. Sawed, scaled, fly cut, milled and chipped crystals and IR transmitting glass will transmit less efficiently, but transmission of optics processed by these means will still be superior to an unpolished crystal blank and will be sufficient for use as sample supporting windows for transmission sampling with spectroscopic analytical instruments.

By using cleaved, fly cut, chipped, milled, scaled or sawed crystals, most of the labor intensive steps required to produce a crystal blank or other optical blank can be eliminated, which significantly reduces the cost of manufacturing the sample supporting window.

Figure 14:
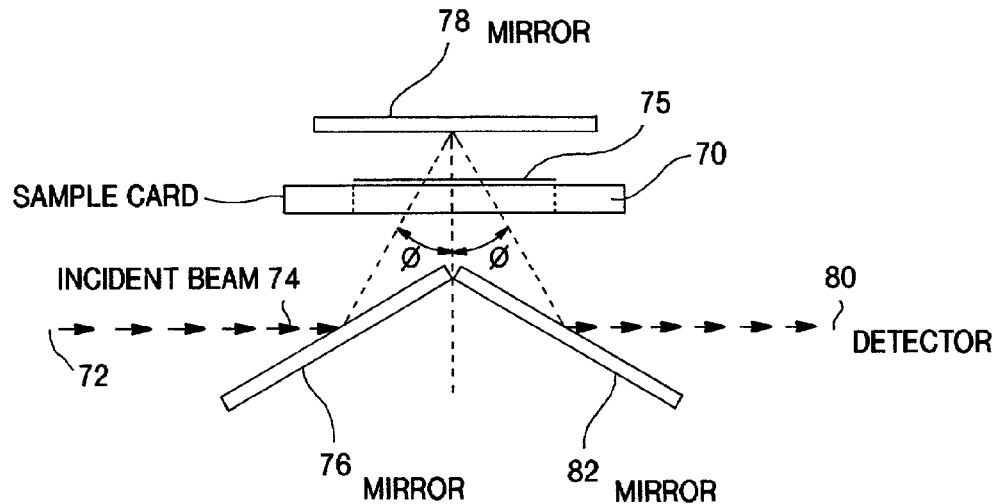
FIG. 14 is a schematic view of the present sample card oriented in a horizontal position within a sample card holding apparatus which mounts in the sample compartment of a spectroscopic analytical instrument.
Figure 15:
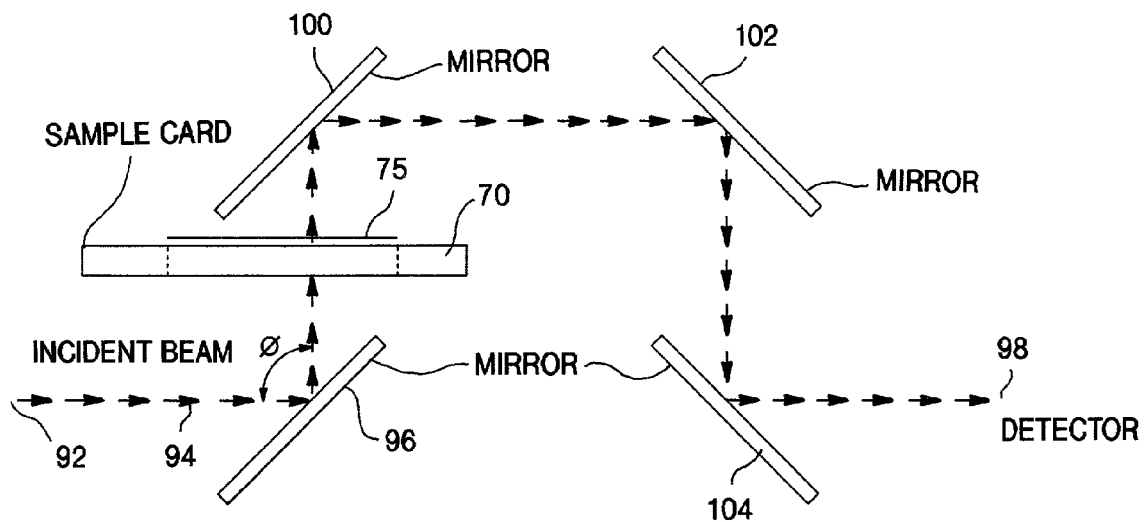
FIG. 15 is a further schematic view of the present sample card oriented horizontally within a sample card holding apparatus which mounts in the sample compartment of a spectroscopic analytical instrument.
Figure 18:
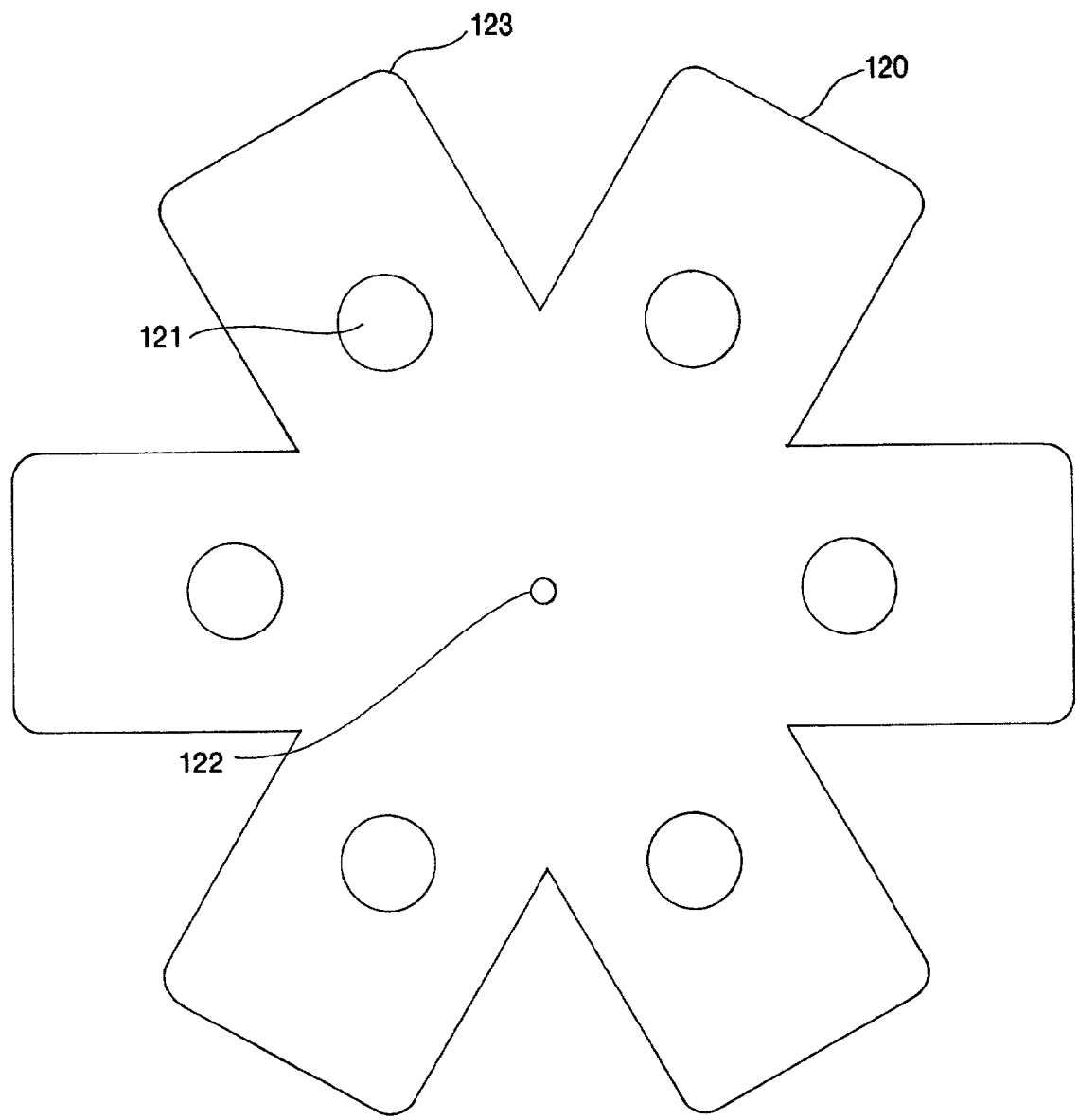
FIG. 18 is a schematic view of the present sample cards in a carousel configuration.

Cleaved alkali halide crystals such as KBr, NaCl and KCl will not fog or haze over as the cleaved faces do not absorb atmospheric moisture. This eliminates packing and handling complications as well as storage limitations, which further reduces manufacturing costs and also makes the product more attractive to customers concerned with storage and handling problems normally associated with hygroscopic precision polished alkali halide crystal optics. In a preferred embodiment of the invention, cleaved infrared transmitting crystal windows are sandwiched between two supporting frames approximately 2" wide. The frames have one or more apertures. The cleaved windows are positioned so that they fill one or more of the apertures in the frames and the apertures are located within the frames so that they will be centered in the beam of a spectrophotometer or other infrared analytical instrument when properly positioned by: (i) placing the assembled frame vertically in a standard spectrometer slide holder; (ii) orienting the frame in a carousel assembly that rotates the sample into the instrument beam; (iii) placing the frame horizontally in an appropriate holder as shown in FIGS. 14 and 15; or (iv) configuring the card as a carousel card with multiple apertures as shown in FIG. 18. Use of cleaved crystal windows is quite inexpensive compared to manufacturing crystal blanks as many labor intensive steps are avoided and issues of handling and humidity control associated with precision optical polishing of these hygroscopic materials are eliminated. Furthermore, the cleaved crystals can be irregularly shaped and yield per boule is very high. NaCl, KCl and KBr alkali halide crystals have a cubic structure, which makes them simple to cleave and ideal for this application. In a preferred embodiment of the invention the crystal sample supporting windows are cleaved from cubic crystals which transmit infrared energy such as alkali halide crystals. In yet another preferred embodiment of the invention, the infrared transmitting crystals sandwiched between the frames within an aperture in the aforesaid manner are fly cut and in yet another embodiment of the invention silica material is fly cut into windows and sandwiched between frames within an aperture in the aforesaid manner. In yet another embodiment of the invention the infrared transmitting crystal or silica windows are scaled; in yet another embodiment of the invention such windows are milled; in yet another embodiment of the invention such windows are sawed; and in yet another embodiment of the invention such windows are chipped. In a preferred embodiment of the invention the fly cut, scaled, milled, sawed and chipped crystal windows are alkali halide crystals, such as KBr, KCl and NaCl. In a preferred embodiment of the invention the fly cut, scaled, milled, sawed and chipped silica windows are fused silica and in yet another preferred embodiment such windows are the material sold under the trademark "AMTIR".

In an another preferred embodiment of the invention, a single surface of an alkali halide crystal window is cleaved along its natural cubic cleavage plane (110). A batch of these cleaved crystals are then mounted, cleaved face down, on a flat surface using a mounting means such as wax or pitch. The faces opposite of the cleaved faces of the crystals are then fly cut using a Bridgeport style milling machine wherein the moving table on which they are mounted in the milling machine is passed under a fly cutter which chips away or scales very fine layers of the crystal surface. The fly cut pieces of such crystals have similar characteristics to those which are cleaved, such as resistance to atmospheric moisture. This method allows the use of scrap material to make crystal windows for IR sampling. The windows fabricated in this manner are sandwiched between frames within an aperture in such frames in the aforesaid manner.

Alkali halide IR transmission crystals have not been sold in cleaved, fly cut, chipped, scaled or sawed form for the practical reasons that (i) they are not cosmetically attractive and (ii) in such form the material has not been significantly advanced towards the next stage of production in the fabrication of a precision optic, which is how these materials have heretofore been used. However, when such materials are mounted in frames to form a sampling card the cosmetic deficiencies are masked and a commercially viable product can be produced. Furthermore, the minor surface imperfections left on the optics are not sufficient to distort qualitative analysis. In fact, with the fly cutting technique, a surface can be produced which is sufficiently flat and transparent to use the optic for high tolerance applications such as lasers, but the process is then much slower and more laborious than the process which is adequate to produce the window quality required for a sample supporting window to be used in a sample card.

Figure 11:
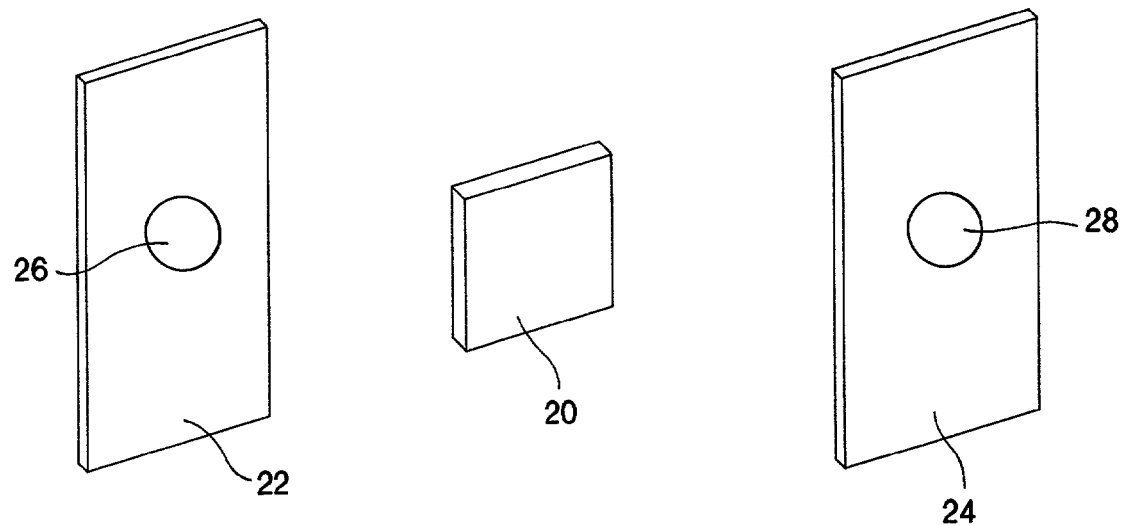
FIG. 11 is an exploded view of a sample card of the present invention with a cleaved crystal window as a sample support.

Use of such cut crystal windows as the sample supporting substrate in a sample card also permits the user to sandwich a liquid or paste sample between two windows. In a preferred embodiment of the invention as shown in FIG. 11, a crystal window 20 cut in accordance with the present invention is sandwiched between cardboard frames 22 and 24, each of which are approximately 2" wide and 3" high, and each of which has a centrally located clear aperture 26, 28 which is filled by the sample supporting window 20 through which the beam of the instrument can be directed. The interior surfaces of the cardboard frames 22, 24 which interface with the sample supporting window 20 are sealed together, preferably, by an adhesive and that adhesive may be a pressure sensitive adhesive that is provided on those interior surfaces. As therefore can be seen, the sample supporting window 20 may have a variety of peripheral configurations, that is, square, rectangular, circular and the like since its perimeter is covered by the frames 22, 24 and thus, there is no need to carefully craft the edge of the window. It is preferred that the support frames 22, 24 be die cut or laser cut from cardboard.

Figure 12:
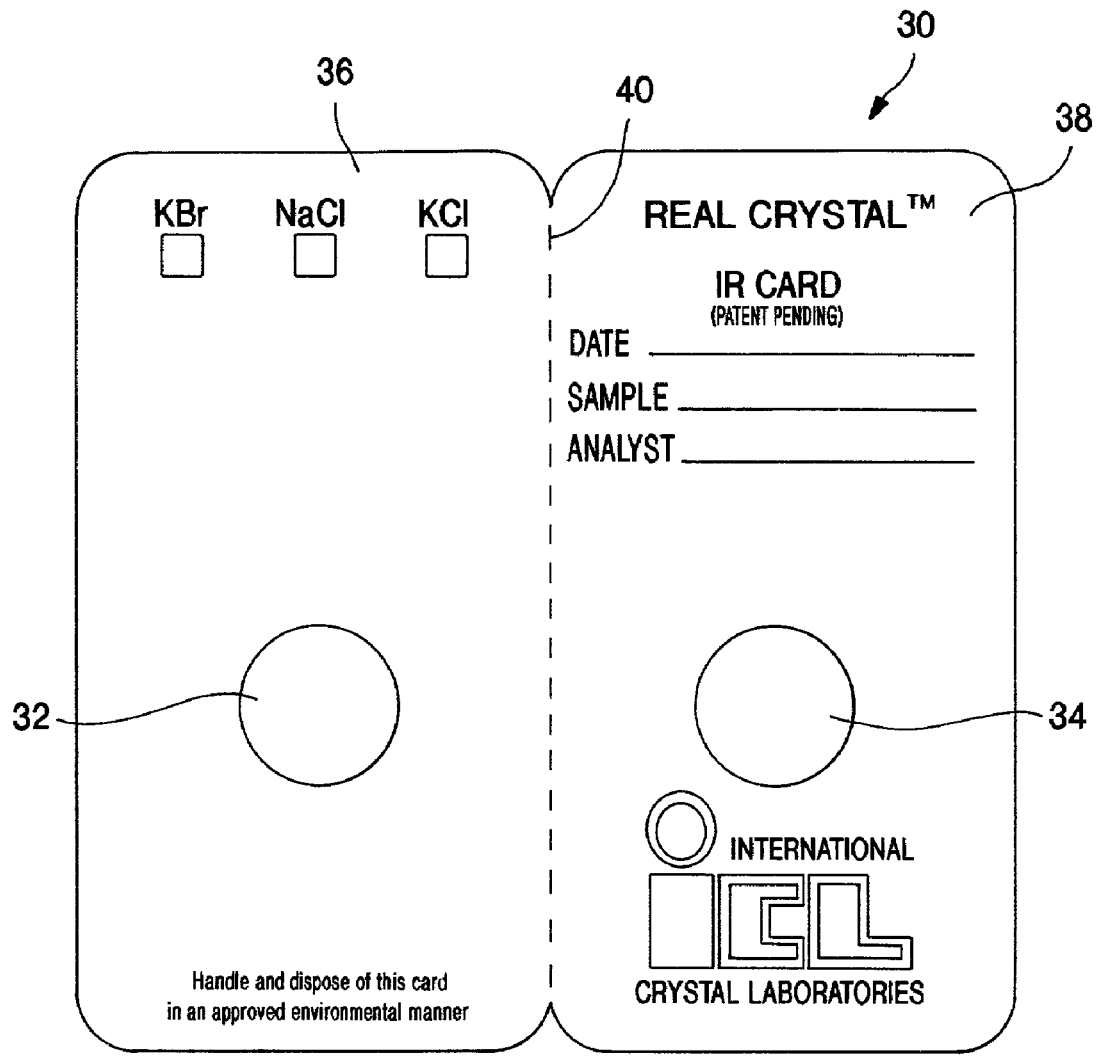
FIG. 12 is a front view of a fold over sample card for sandwiching a sample support window.

Turning now to FIG. 12, there is shown a front view of an alternative embodiment of a sample card 30. In this embodiment, the sample card 30 is die cut or laser cut from single piece of cardboard. The internal surfaces of the card (not shown), which are facing away in the FIG., are coated with pressure sensitive adhesive. Thus, with this embodiment, there are two apertures 32, 34, and there are two identical mirror image halves, 36, 38 with a central spine 40 defining each half, such that when the single piece of the sample card 30 is folded in half vertically along the central spine 40, the crystal or infrared transmitting glass sample supporting window prepared as described herein can be sandwiched between the two halves 36, 38 since the two apertures 32, 34 are in alignment. As a further embodiment, there may be plurality of apertures formed in the halves 36, 38.

In another embodiment of the invention, the crystal or silica sample supporting window of the present invention is sandwiched between a metal plate and a magnet, each of which has a clear aperture which is filled by the window through which the beam of the spectroscopic analytical instrument can be directed.

Figure 13:
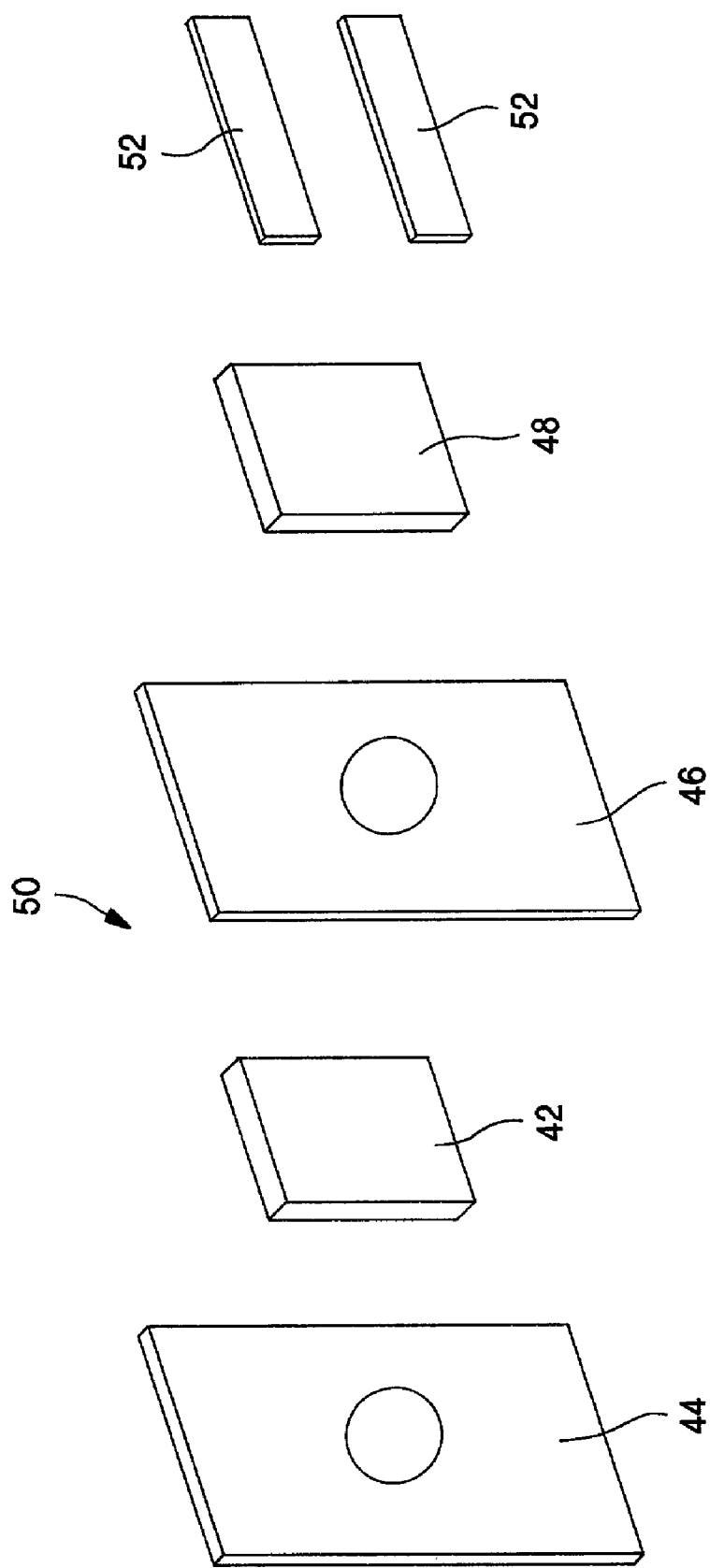
FIG. 13 is an exploded view of a sample care with a cleaved crystal support an a second cover window.

Turning now to FIG. 13, there is shown an exploded view of a further embodiment of the present invention. In this embodiment, there is a first sample supporting window 42 sandwiched between two cardboard frames 44, 46 in the manner described with respect to the FIG. 11 embodiment, and a second cover slide window 48 and means for holding such second cover slide window 48 in place to sandwich a sample between such first window 42 and the second window 48 to make up the overall sample card assembly 50. Both the first and second windows 42 and 48 are prepared in accordance with the present invention, but in yet another embodiment of the invention the window cover slide 48 is prepared in accordance with traditional precision optical polishing techniques. The second cover slide window 48 is secured and held to the sample card 50. One such means of securing the cover slide window 48 may be by supports 52 coated with pressure sensitive adhesive on the portion of the supports which contact the cardboard frame but without any adhesive on the portion of the supports 52 which interface with the second cover slide window 48. Alternatively, the second substrate 48 may be supported by means of a magnet with a clear aperture which is used in conjunction with a metal plate with a clear aperture placed behind the sample card 50 or which metal plate serves as the sample card 50. In yet another embodiment, the second window 48 can be retained in place by means of the fiber and hook combination material sold under the trademark VELCRO. In still another embodiment, a spacer with a centrally located clear aperture can be placed between the first sample supporting window 42 and the second cover slide window 48 to define the thickness of the sample which is placed between the two windows.

The method of using any of the aforedescribed sample cards for infrared sampling is by placing a liquid, paste, powder or solution sample on one or more of the sample supporting windows of the sample card and then placing the sample card vertically into the universal slide mount of a spectrophotometer or other spectroscopic analytical instrument such as a filtrometer. In yet another embodiment of the invention the sample prepared as aforesaid is placed in an spectroscopic analytical instrument horizontally using a device of the type shown in FIG. 14 or FIG. 15, and in yet another embodiment of the invention sample cards are inserted in a carousel configuration in a holder of the type shown in FIGS. 16 and 17. One or more scans are then taken of the sample with the instrument. Alternatively, a solution is allowed to dry so that all of the solvent is removed from the sample and one or more scans are taken of the remaining sample with the instrument. In another embodiment of the method, the sample card is placed in an FTIR spectrophotometer or other spectroscopic analytical instrument prior to applying the sample to the substrate for taking a sample scan, and one or more background scans are taken of the sample support substrate which are stored for subtraction from the sample scans. As a yet further embodiment, a sample can be mixed with or ground into a liquid such as mineral oil. Prior to placing the sample mixed with the liquid, such as mineral oil, onto the crystal sample supporting window of the sample card, a sample of the liquid, such as mineral oil, is placed on the substrate and one or more background scans are taken of both the substrate and such liquid which are stored for subtraction from the sample scans. As yet a further embodiment, a sample such as a bacterial colony is placed directly onto the crystal sample supporting window of the sample card and covered with a cover slide window. Such a sample is then placed into a spectroscopic analytical instrument for analysis, after the sample has cured for an appropriate length of time.

In FIG. 14, there is shown a schematic view of the use of a sample card 70 constructed in accordance with the present invention and where the sample card is placed within a device which is capable of reflecting the instrument beam through the aperture in the card which contains the sample supporting window and the sample card oriented in the horizontal position. Thus, as seen in FIG. 14, the sample card 70 is placed in the horizontal position within an instrument having an energy or light source 72. The incident beam of energy or light 74 is also horizontal. The incident beam is directed to the sample card 70 by a mirror 76 that is placed at an angle theta (e.g.

about 30 degrees) and then back through the sample card 70 by a second mirror 78 which returns the beam to the same level as the incident beam and then reflected by mirror 82 so that it can be directed to a detector 80. In this embodiment of the invention the energy beam passes through the sample 75 twice, which results in more intense absorbance peaks than if the beam only passed through the sample 75 once.

In a further embodiment, shown in the schematic view of FIG. 15, the energy beam only passes through the horizontally positioned sample 75 once. As can be seen, the sample card 70 constructed in accordance with the present invention, is placed in the horizontal position within an instrument having an energy or light source 92. The beam of incident beam energy of light 94 is also horizontal. The incident beam is directed to the sample card 70 by a mirror 96 that is placed at an angle theta (e.g. about 45 degrees) and then back to the level of the incident beam 94 and on to a detector 98 by a second mirror 100 and a third mirror 102 which returns the beam to the same level as the incident beam. A fourth mirror 104 then directs the beam of energy to the detector 98. In this embodiment of the invention, the energy beam passes through the sample 75 only once which results in less intense absorbance peaks than would be the case if the beam passes through the sample twice as was shown in the embodiment shown in FIG. 14 and the results will be comparable to traditional transmission sampling with the sample oriented vertically in the spectroscopic analytical instrument.

It is understood that first surface mirrors should be used as shown in FIGS. 14 and 15 so that no spurious absorbances are detected from the non reflected material comprising the mirror.

Figure 16:
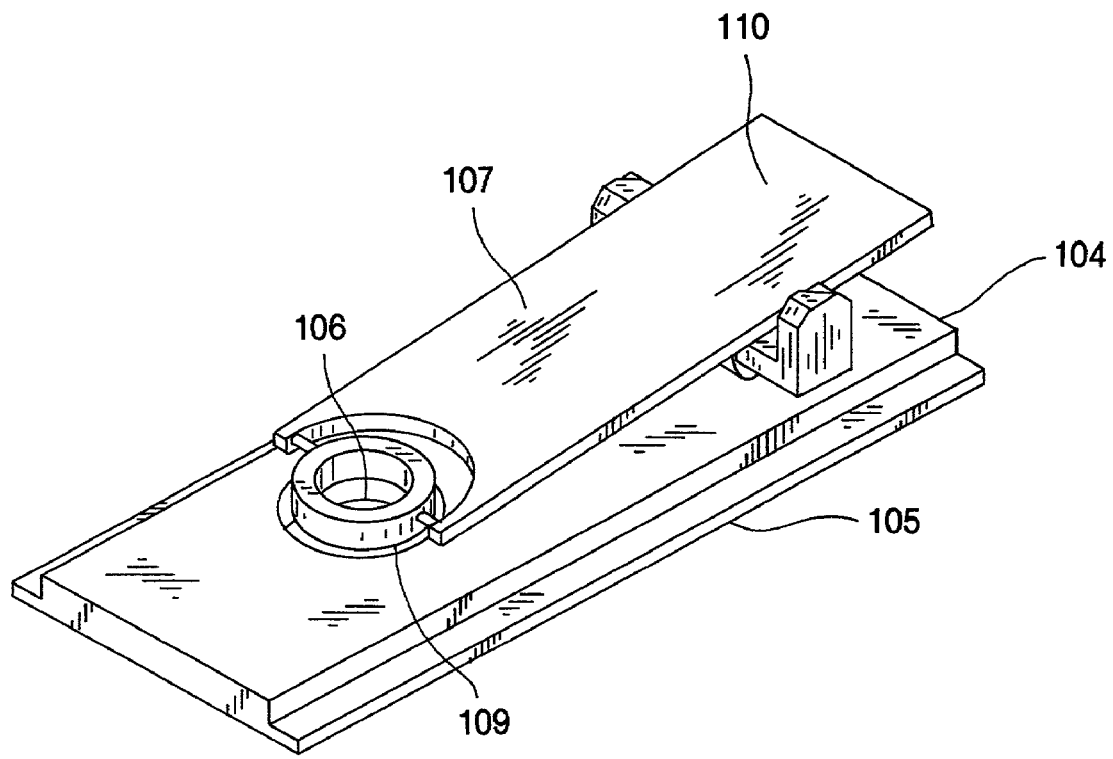
FIG. 16 is a schematic view of an apparatus for holding a cover slip window on top of a sample supporting window to sandwich a sample between the windows.
Figure 17:
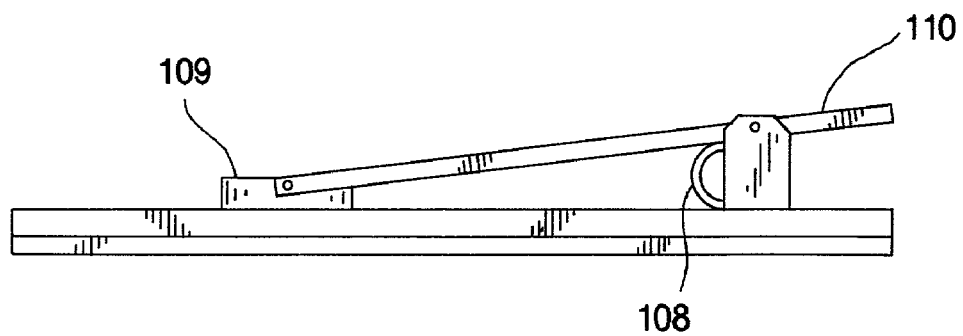
FIG. 17 is a further schematic view of an apparatus for holding a cover slip window on top of a sample supporting window to sandwich a sample between the windows.

In FIGS. 16 and 17 there is shown another embodiment of the method in which cover slide windows 48 as shown in FIG. 13 are held in place and in contact with the window sample supporting substrate 42 by clamping means. A sample card is mounted in a clamp 104 comprising a back plate 105 with a clear aperture 106 as large as the aperture in the sample card 11, 12, 13, 70 and with a moveable clamping armature 107 which is controlled by a spring 108 much like a spring loaded clothes pin. The clamping armature 107 is opened by pressing on the high end 110 thereof to overcome the tension of the spring 108. The spring 108 applies downward pressure on the clamping armature 1105 and against the cover slide window (not shown), the sample (not shown) and the sample supporting window (not shown) which is sandwiched between the end of the clamping arm 109 and the back plate 105. The end of the clamping arm 109 also contains a clear aperture which is slightly smaller than the outside perimeter of the cover slide window 48 so as to enable the energy beam of a spectroscopic analytical instrument to pass through while also applying pressure to the perimeter of the face of the cover slide window 48. The back plate 105 is of a size and geometry that will fit the standard slide mount contained in an infrared spectrophotometer or other spectroscopic analytical instrument. In another embodiment of the invention a sample card 30 with a sample sandwiched between a sample supporting window 42 and cover slide window 48 the clamp 104 is inserted into a device (not shown) which orients several clamps in a carousel configuration and rotates the clamps 104 and the samples and sample cards clamped thereon into and out of the beam of a spectroscopic analytical instrument.

In FIG. 18 there is shown a sample card 120 in a carousel configuration. The sample supporting windows 121 are mounted in the sample card by sandwich means in the same manner as described in FIGS. 11, 12 and 13. The sample supporting windows are mounted in a circular pattern around a central aperture 122. It is understood that there could be concentric circles (not shown) of sample supporting windows 121. Samples are placed on the sample supporting windows in the same manner as hereinabove described in the case of the method of using sample cards in other geometries. As shown, the sample card has rounded corners 123 to facilitate the use of pressure sensitive adhesive on the rear surfaces of the cards by making it easier to peel the protective cover off of the pressure sensitive adhesive, but it is understood that the outside geometry of a such sample card in a carousel configuration sample card configuration could be other shapes including but not limited to round, square, hexagon, pentagon or octagon. Sample cards in the carousel configuration can be used both with and without cover slide windows and it is understood as discussed above that the carousel can be created by mechanical means using individual sample cards mounted in an apparatus to create a carousel. The carousel sample card 120 or other carousel creating device containing samples to be analysed is mounted in a spectroscopic analytical instrument and by rotating means the clear apertures 121 containing the sample supporting windows 20, 42 and the sample (not shown) are rotated into and out of the beam of the instrument for a time sufficient to scan the sample by detecting absorbance by the sample of the energy emitted by the instrument.

It is understood that the instrument in which a sample card 11, 12, 13, 70, 120 or the device holding the sample card 104 is placed, whether vertically or horizontally 70, may be an FTIR microscope as well as an IR or FTIR spectrophotometer or any other type of spectroscopic analytical instrument It is further understood that the invention is equally applicable to other fields of spectroscopy, including UV, NIR, VIS as well as to fixed band pass filtrometers know as "infracal" devices.

While the present invention has been set forth in terms of a specific embodiment or embodiments, it will be understood that the present invention herein disclosed may be modified or altered by those skilled in the art to other configurations. Accordingly, the invention is to be broadly construed and limited only by the scope and spirit of the claims appended hereto.

I claim:

1. A sample holder for use with an infrared spectrophotometer or infrared filtometer that analyzes a sample through which infrared light is transmitted comprising a mounting means comprised of a first material having an aperture formed therein, an infrared light transmitting alkali halide crystal sample supporting substrate being present in the aperture comprised of a second material allowing infrared light to pass therethrough without the infrared light transmitting alkali halide crystal sample supporting substrate or any other material within the aperture substantially absorbing infrared light within a substantial portion of the infrared spectral range, said infrared light transmitting alkali halide crystal sample supporting substrate being formed by one or more of the steps comprising cleaving, fly cutting, chipping, milling, or scaling.

2. The sample holder as defined in claim 1 wherein said infrared light transmitting alkali halide crystal sample supporting substrate is an alkali halide crystal.

3. The sample holder as defined in claim 1 wherein said infrared light transmitting alkali halide crystal sample supporting substrate is an alkali halide crystal selected from the group consisting of KBr, NaCl and KCl.

4. The sample holder as defined in claim 1 wherein said infrared light transmitting alkali halide crystal sample supporting substrate is mounted in the holder such that the perimeter of the aperture frames all or a centrally located part of said infrared light transmitting alkali halide crystal sample supporting substrate to form an unimepeded path for infrared light to pass through the infrared light transmitting sample supporting substrate.

5. The sample holder as defined in claim 4 further having an infrared light transmitting cover slide window formed by one or more of the steps comprising cleaving, fly cutting, chipping, milling, or scaling.

6. The sample holder as defined in claim 5 wherein a spacer is located between said infrared light transmitting alkali halide crystal sample supporting substrate and said infrared light transmitting cover slide window to create a predetermined space therebetween.

7. The sample holder as defined in claim 5 wherein said infrared light transmitting cover slide window is affixed to said infrared light transmitting crystal sample supporting substrate by a clamping means.

8. A method for the manufacture of a sample holder for use in an infrared spectrophotometer or infrared filtometer, said method comprising the steps of:
    providing a mounting means comprised of a first material having an aperture therethrough;
    providing an infrared light transmitting alkali halide crystal material,
    forming an infrared light transmitting alkali halide crystal sample supporting substrate of a second material having infrared light transmissive properties such that the substrate does not substantially absorb infrared light within a substantial portion of the infrared spectral range, said infrared light transmitting alkali halide crystal sample supporting substrate being formed by cleaving, fly cutting, chipping, milling, or scaling material from said infrared light transmitting alkali halide crystal material to form an infrared light transmitting alkali halide crystal sample supporting substrate that allows the passage of infrared light therethrough;
    positioning the infrared light transmitting alkali halide crystal sample supporting substrate within the aperture so as to allow infrared light to pass through the aperture and the infrared light transmitting alkali halide crystal sample supporting substrate and with no other material within the aperture that absorbs infrared light.

9. A method for the manufacture of a sample holder as defined in claim 8 wherein said step of providing a mounting means having an aperture comprises providing a disposable card or demountable card.

10. A method for the manufacture of a sample holder as defined in claim 8 further including the step of:
    mounting the infrared light transmitting alkali halide crystal sample supporting substrate to the holder in a position wherein all or a centrally located part of the infrared light transmitting alkali halide crystal sample supporting substrate is framed by the perimeter of said aperture.

11. A method for the manufacture of a sample holder as defined in claim 8 further including the step of affixing an infrared light transmitting cover slide window to the infrared light transmitting alkali halide crystal sample supporting substrate to provide a means of sandwiching a sample between said infrared light transmitting cover slide window and said infrared light transmitting alkali halide crystal sample supporting substrate.

12. A method for using a sample holder in an infrared spectrophotometer or infrared filtometer having an infrared light source and an infrared light detector, said method comprising the steps of:
    providing an infrared light transmitting alkali halide crystal material,
    providing an infrared light transmitting alkali halide crystal sample supporting substrate comprised of a first material having infrared light transmissive properties such that the infrared light transmitting alkali halide crystal substrate does not substantially absorb infrared light within a substantial portion of the infrared spectral range, said infrared light transmitting alkali halide crystal sample supporting substrate being formed by cleaving, fly cutting, chipping, milling, or scaling the infrared light transmittng alkali halide crystal sample supporting substrate from said infrared light transmitting alkali halide crystal material,
    providing a mounting means comprised of a second material having at least one aperture adapted to fit within the spectrophotometer or filtometer, said mounting means being formed so as to be capable of orienting the infrared light transmitting alkali halide crystal sample supporting substrate in the path of the infrared light emitted by an infrared spectrophotometer or filtometer,
    mounting the infrared light transmitting alkali halide crystal sample supporting substrate to the mounting means in a position where all or a centrally located part of the infrared light transmitting alkali halide crystal sample supporting substrate is framed by the perimeter of the at least one aperture,
    placing a sample to be analyzed onto the infrared light transmitting alkali halide crystal sample supporting substrate,
    inserting the holder into the spectrophotometer or filtometer between the infrared light source and the infrared light detector with the at least one aperture aligned with the infrared light emitted by the infrared light source to allow the passage of infrared light though the sample, the infrared light transmitting alkali halide crystal sample supporting substrate and the aperture and no other material within said aperture other than the sample that absorbs infrared light.

13. A method as defined in claim 12 wherein said step of providing a mounting means comprises providing a card made of a disposable material.

14. A method as defined in claim 13 wherein said step of providing an infrared light transmitting material comprises providing a material selected from the group consisting of KBr, NaCl and KCl.

15. A method as defined in claim 13 wherein said step of providing a mounting means further comprises the step of affixing an infrared light transmitting cover slide window to the infrared light transmitting alkali halide crystal sample supporting substrate to form a means of sandwiching a sample between said infrared light transmitting cover slide window and said infrared light transmitting alkali halide crystal sample supporting substrate, said infrared light transmitting cover slide window being formed by one or more of the steps comprising cleaving, fly cutting, chipping, milling, or scaling without precision optical polishing of the infrared light transmitting cover slide window.

16. A method as defined in claim 15 wherein said step of placing a sample to be analyzed comprises sandwiching the sample between the infrared light transmitting cover slide window and the infrared light transmitting alkali halide crystal sample supporting.

17. A method as defined in claim 16 wherein said step placing a sample to be analyzed comprises placing a bacterial colony between said infrared light transmitting cover slide window and said infrared light transmitting alkali halide crystal sample supporting substrate.

18. A method for using a sample holder for use in an infrared spectrophotometer or infrared filtometer having an infrared light source and an infrared light detector, said method comprising the steps of
providing a mounting means comprised of a first material having a plurality of apertures adapted to fit within said infrared spectrophotometer or infrared filtometer, said mounting means being formed so as to be capable of orienting the apertures in the path of the infrared light emitted by an infrared spectrophotometer or filtometer,
providing an infrared light transmitting alkali halide crystal material,
forming a plurality of infrared light transmitting alkali halide crystal sample supporting substrates comprised of a second material having infrared light transmissive properties such that the substrate does not substantially absorb infrared light within a substantial portion of the infrared spectral range, said infrared light transmitting alkali halide crystal sample supporting substrate being formed by cleaving, fly cutting, chipping, milling or scaling said infrared light transmitting crystal sample supporting substrates from said light transmitting material,
mounting one of said plurality of said infrared light transmitting alkali halide crystal sample supporting substrates to the mounting means in a position wherein all or a centrally located part of one of said infrared light transmitting alkali halide crystal sample supporting substrates is framed by the perimeter of at least one of the apertures,
placing a sample to be analyzed onto at least one of the infrared light transmitting alkali halide crystal sample supporting substrates,
inserting the holder having the infrared light transmitting alkali halide crystal sample supporting substrate mounted thereto into said infrared spectrophotometer or infrared filtometer between the infrared light source and the infrared light detector with at least one of the apertures aligned with the infrared light emitted by the infrared light source to allow the passage of a beam of infrared light though one or more samples, said infrared light transmitting alkali halide crystal sample supporting substrates and apertures and no other material other than the sample within said aperture that absorbs infrared light.

19. A method for using a sample holder as defined in claim 18 wherein said step of forming a plurality of apertures and infrared light transmitting alkali halide crystal sample supporting substrates mounted thereon comprises forming the plurality of apertures and infrared light transmitting sample supporting substrates in a carousel configuration.

20. A method for using a sample holder as defined in claim 19 wherein said step of placing a sample to be analyzed comprises placing a plurality of samples onto said plurality of infrared light transmitting alkali halide crystal sample supporting substrates and said infrared spectrophotometer or infrared filtometer passes infrared light sequentially through said plurality of samples, said infrared light transmitting alkali halide crystal sample supporting substrates and said apertures and no other material within said apertures that absorbs infrared light.

21. A method for using a sample holder as defined in claim 19 wherein said step of placing a sample onto at least one of the infrared light transmitting alkali halide crystal sample supporting substrates comprises placing a bacterial colony onto said at least one infrared light transmitting sample supporting substrate.

22. A method for using a sample holder as defined in claim 19 wherein said step of inserting the holder having the infrared light transmitting alkali halide crystal sample supporting substrate mounted thereto into the infrared spectrophotometer or infrared filtometer comprises inserting the holder in a horizontal position within the infrared spectrophotometer or infrared filtometer and passing a beam of infrared light at least once through the sample, the infrared light transmitting alkali halide crystal sample supporting substrates and the aperture.

23. A method for using a sample holder as defined in claim 22 wherein the beam of infrared light is passed at least once through the sample by means of reflection.

24. A method for using a sample holder for use in an infrared spectrophotometer or infrared filtometer having an infrared light source and an infrared light detector, said method comprising the steps of:
providing a plurality of mounting means comprised of a first material, each having at least one aperture, each of said mounting means being formed so as to be capable of orienting the at least one aperture in the path of the infrared light emitted by an infrared spectrophotometer or filtometer
providing an infrared light transmitting alkali halide crystal material,
forming a plurality of infrared light transmitting alkali halide crystal sample supporting substrates comprised of a second material having infrared light transmissive properties such that the infrared light transmitting substrates do not substantially absorb infrared light within a substantial portion of the infrared spectral range, said infrared light transmitting alkali halide crystal sample supporting substrates formed by cleaving, fly cutting, chipping, milling, or scaling infrared light transmitting alkali halide crystal sample supporting substrates from said infrared light transmitting crystal material,
mounting one of said plurality of infrared light transmitting alkali halide crystal sample supporting substrates to each of said plurality of mounting means in a position wherein all or a centrally located part of said sample supporting mounting means is framed by the perimeter of an apertures,
providing a mechanical carousel adapted to fit into the infrared spectrophotometer or infrared filtometer,
mounting said plurality of mounting means onto the mechanical carousel,
placing a sample to be analyzed onto at least one of the infrared light transmitting alkali halide crystal sample supporting substrates,
inserting the carousel into the infrared spectrophotometer or infrared filtometer between the infrared light source and the infrared light detector with the at least one aperture aligned with the infrared light emitted by the infrared light source to allow the passage of infrared light in a sequential manner through the plurality of infrared light transmitting alkali halide crystal sample supporting substrates, said samples and said apertures and no other material other that the samples within said apertures that absorb infrared light.

25. A method for using a sample holder in an infrared spectrophotometer or infrared filtometer having an infrared light source and an infrared light detector, said method comprising the steps of:
providing an infrared light transmitting alkali halide crystal material,
providing an infrared light transmitting alkali halide crystal sample supporting substrate comprised of a second material having infrared light transmissive properties such that the infrared light transmitting alkali halide crystal sample supporting substrate does not substantially absorb infrared light within a substantial portion of the infrared spectral range, said infrared light transmitting alkali halide crystal sample supporting substrate formed by cleaving, fly cutting, chipping, milling or scaling the infrared light transmitting alkali halide crystal sample supporting substrate from said infrared light transmitting alkali halide crystal material, providing a mounting means comprised of a first material having at least one aperture adapted to fit within the infrared spectrophotometer or infrared filtometer, said holder being formed so as to be capable of orienting the at least one aperture in the path of the infrared light emitted by an infrared spectrophotometer or filtometer, mounting the infrared light transmitting alkali halide crystal sample supporting substrate to the mounting means in a position wherein all or a centrally located part of the infrared light transmitting alkali halide crystal sample supporting substrate is framed by the perimeter of the at least one aperture, inserting the holder into the infrared spectrophotometer or infrared filtometer to allow the passage of a beam of infrared light though the infrared light transmitting alkali halide crystal sample supporting substrate to obtain one or more a background scans of the absorbance of the infrared light transmitting alkali halide crystal sample supporting supporting substrate, placing a sample to be analyzed onto the infrared light transmitting alkali halide crystal sample supporting substrate, inserting the holder into the infrared spectrophotometer or infrared filtometer between the infrared light source and the infrared light detector with the at least one aperture aligned with the infrared light emitted by the infrared light source to allow the passage of infrared light though the infrared light transmitting alkali halide crystal sample suporting substrate and the sample located thereon and with no other material within said at least one aperture that absorbs infrared light to obtain a scan of the absorbance of the sample and the infrared light transmittting alkali halide crystal sample supporting substrate, and, using the one or more background scans to subtract the background absorbance of the infrared light transmitting alkali halide crystal sample supporting substrate without the sample from the absorbance of the sample and the infrared light transmitting alkali halide crystal sample supporting substrate.

26. A method for using a sample holder in an infrared spectrophotometer or infrared filtometer having an infrared light source and an infrared light detector, said method comprising the steps of:

providing an infrared light transmitting alkali halide crystal material, providing an infrared light transmitting alkali halide crystal sample supporting substrate comprised of a second material having infrared light transmissive properties such that the infrared light transmitting alkali halide crystal sample supporting substrate does not substantially absorb infrared light within a substantial portion of the infrared spectral range, said infrared light transmitting alkali halide crystal sample supporting substrate formed by cleaving, fly cutting, chipping, milling or scaling the infrared light transmitting alkali halide crystal sample supporting substrate from said infrared light transmitting alkali halide crystal material, providing a mounting means comprised of a first material having at least one aperture adapted to fit within the infrared spectrophotometer or infrared filtometer, said mounting means being formed so as to be capable of orienting the infrared light transmitting alkali halide crystal sample supporting substrate in the path of the infrared light emitted by the infrared spectrophotometer or filtometer, mounting the infrared light transmitting alkali halide crystal sample supporting substrate to the mounting means in a position wherein all or a centrally located part of the infrared light transmitting alkali halide crystal sample supporting substrate is framed by the perimeter of the at least one aperture, placing a medium onto the infrared light transmitting alkali halide crystal sample supporting substrate with which a sample will be mixed, inserting the holder into the infrared spectrophotometer or infrared filtometer to allow the passage of a beam of infrared light though the medium and the infrared light transmitting alkali halide crystal sample supporting substrate to obtain one or more a background scans of the infrared light transmitting alkali halide crystal sample supporting substrate and the medium, placing a sample to be analyzed mixed with the medium onto the infrared light transmitting alkali halide crystal sample supporting substrate, inserting the holder into the infrared spectrophotometer or infrared filtometer analytical instrument between the infrared light source and the infrared light detector with the at least one aperture aligned with the infrared light emitted by the infrared light source to allow infrared light though the infrared light transmitting alkali halide crystal sample supporting substrate and the medium mixed with the sample and with no other material other than the sample within said at least one aperture that absorbs infrared light and, using the one or more background scans to subtract the absorbances of the medium and the infrared light transmitting alkali halide crystal sample supporting substrate from the absorbances of the medium, the infrared light transmitting alkali halide crystal sample supporting substrate and the sample.

27. A method of using a sample holder as defined in claim 26 wherein said step of placing a medium onto the infrared transmitting alkali halide crystal sample supporting substrate with which the sample will be mixed comprises placing mineral oil on the infrared transmitting alkali halide crystal sample supporting substrate.

28. A method of using a sample holder as defined in claim 26 wherein said step of placing a medium onto the infrared light transmitting alkali halide crystal sample supporting substrate with which the sample will be mixed comprises placing a solvent on the infrared light transmitting alkali halide crystal sample supporting substrate.

29. A method of using a sample holder as defined in claim 26 wherein said step of placing a medium onto the infrared light transmitting alkali halide crystal sample supporting substrate with which the sample will be mixed comprises placing a mixture of KBr powder and a solvent or a mineral oil on the infrared light transmitting alkali halide crystal sample supporting substrate.

30. A method of using a sample holder as defined in claim 26 wherein said step of placing a medium onto the infrared light transmitting alkali halide crystal sample supporting substrate with which the sample will be mixed comprises placing an alkali halide crystal powder on the infrared light transmitting alkali halide crystal sample supporting substrate.

31. A method of using a sample holder as defined in claim 30 wherein said step of placing a medium onto the infrared light transmitting alkali halide crystal sample supporting substrate with which the sample will be mixed comprises placing KBr powder on the infrared light transmitting alkali halide crystal sample supporting substrate.

32. A method for using a sample holder in an infrared spectrophotometer or infrared filtometer having an infrared light source and an infrared light detector, said method comprising the steps of:

provided an infrared light transmitting alkali halide crystal material, providing an infrared light transmitting alkali halide crystal sample supporting substrate comprised of a second material having infrared light transmissive properties such that the infrared light transmitting alkali halide crystal sample supporting substrate does not substantially absorb infrared light within a substantial portion of the infrared spectral range, said infrared light transmitting alkali halide crystal sample supporting substrate formed by cleaving, fly cutting, chipping, milling or scaling the infrared light transmitting alkali halide crystal sample supporting substrate from said infrared light transmitting alkali halide crystal material, providing a mounting means comprised of a first material having at least one aperture adapted to fit within the spectrophotometer or filtometer, said mounting means being formed so as to be capable of orienting the infrared light transmitting sample supporting substrate in the path of the infrared light emitted by an infrared spectrophotometer or filtometer, mounting the infrared light transmitting 1 sample supporting substrate to the mounting means in a position where all or a centrally located part of the infrared light transmitting alkali halide crystal sample supporting substrate is framed by the perimeter of the at least one aperture, placing a bacterial colony to be analyzed onto the infrared light transmitting alkali halide crystal sample supporting substrate, inserting the mounting means into the spectrophotometer or filtometer between the infrared light source and the infrared light detector with the at least one aperture aligned with the infrared light emitted by the infrared light source to allow the passage of infrared light though the bacterial colony, the infrared light transmitting alkali halide crystal sample supporting substrate and the at least one aperture and with no other material other than the bacterial colony within said at least one aperture that absorbs infrared light.

* * * * *